United States Patent
Hedmann et al.

(10) Patent No.: US 9,555,181 B2
(45) Date of Patent: Jan. 31, 2017

(54) MEDICAL DEVICE HEATERS AND METHODS

(71) Applicant: Fresenius Medical Care Deutschland GmbH, Bad Homburg (DE)

(72) Inventors: Frank L. Hedmann, Volkach (DE);
Sven Sebesta, Schweinfurt (DE);
Ulrich Wernicke, Theres (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 14/179,646

(22) Filed: Feb. 13, 2014

(65) Prior Publication Data
US 2014/0180200 A1 Jun. 26, 2014

Related U.S. Application Data

(63) Continuation of application No. 13/315,240, filed on Dec. 8, 2011, now Pat. No. 8,692,167.
(Continued)

(51) Int. Cl.
*H05B 1/02* (2006.01)
*A61M 1/28* (2006.01)
(Continued)

(52) U.S. Cl.
CPC ............ *A61M 1/28* (2013.01); *A61M 1/1664* (2013.01); *A61M 5/44* (2013.01); *A61M 2205/12* (2013.01); *A61M 2205/3653* (2013.01)

(58) Field of Classification Search
CPC ....... H05B 1/02; H05B 1/0202; H05B 1/0241; H05B 3/0066; H05B 3/0085; H05B 1/025; G03G 15/0266; C03G 15/003; C03G 15/2039; C03G 15/205; C03G 15/2053; C03G 15/304; H25J 3/00
(Continued)

(56) References Cited

U.S. PATENT DOCUMENTS 1,406,372 A 12/1921 Grapp
1,689,432 A 12/1927 Hartwig
(Continued)

FOREIGN PATENT DOCUMENTS

AU 9184982 6/1983
DE 2618415 A1 11/1977
(Continued)

OTHER PUBLICATIONS

Acumen, "Acute Dialysis Machine Brief Operating Instructions," Software Version 1.0, pp. 1-146, Jan. 1996.
(Continued)

*Primary Examiner* — Mark Paschall
(74) *Attorney, Agent, or Firm* — Fish & Richardson P.C.

(57) ABSTRACT

A medical device having a heater with at least one heating element which has mains voltage applied to it by a heating control unit. The heating control unit includes a monitoring arrangement and a switching arrangement. The monitoring arrangement can recognize the zero crossings of the mains voltage, and the switching arrangement can switch the at least one heating element on or off in the zero crossing. The heating control unit controls the power of the heating by switching on and off of one or more half cycles of the mains AC voltage.

25 Claims, 13 Drawing Sheets

Related U.S. Application Data

(60) Provisional application No. 61/421,332, filed on Dec. 9, 2010.

(51) Int. Cl.
*A61M 5/44* (2006.01)
*A61M 1/16* (2006.01)

(58) Field of Classification Search
USPC ....... 219/505, 216, 492, 497, 508, 483–486; 323/319, 235, 236
See application file for complete search history.

(56) References Cited

U.S. PATENT DOCUMENTS

| | | | |
|---|---|---|---|
| 2,107,173 A | 2/1938 | Bauer | |
| 3,130,289 A | 4/1964 | Katzman et al. | |
| 3,524,078 A * | 8/1970 | Harris, Jr. | 327/455 |
| 3,694,625 A | 9/1972 | Cole | |
| 3,808,401 A | 4/1974 | Wright et al. | |
| 3,927,955 A | 12/1975 | Spinosa et al. | |
| 3,985,135 A | 10/1976 | Carpenter et al. | |
| 4,026,669 A | 5/1977 | Leonard et al. | |
| 4,046,991 A * | 9/1977 | Sefton et al. | 219/497 |
| 4,303,376 A | 12/1981 | Siekmann | |
| 4,314,143 A | 2/1982 | Bilstad et al. | |
| 4,370,983 A | 2/1983 | Lichtenstein | |
| 4,374,321 A * | 2/1983 | Cunningham et al. | 219/497 |
| 4,382,753 A | 5/1983 | Archibald | |
| 4,436,620 A | 3/1984 | Bellotti et al. | |
| 4,453,932 A | 6/1984 | Pastrone | |
| 4,479,762 A | 10/1984 | Bilstad et al. | |
| 4,486,189 A | 12/1984 | Troutner et al. | |
| 4,623,328 A | 11/1986 | Hartranft | |
| 4,628,186 A | 12/1986 | Bergemann et al. | |
| 4,628,499 A | 12/1986 | Hammett | |
| 4,634,843 A * | 1/1987 | Payne | 219/486 |
| 4,643,713 A | 2/1987 | Viitala | |
| 4,657,490 A | 4/1987 | Abbott | |
| 4,662,906 A | 5/1987 | Matkovich et al. | |
| 4,666,598 A | 5/1987 | Heath et al. | |
| 4,676,467 A | 6/1987 | Palsulich | |
| 4,710,166 A | 12/1987 | Thompson et al. | |
| 4,716,520 A | 12/1987 | Locke et al. | |
| 4,778,451 A | 10/1988 | Kamen | |
| 4,798,090 A | 1/1989 | Heath et al. | |
| 4,808,161 A | 2/1989 | Kamen | |
| 4,826,482 A | 5/1989 | Kamen | |
| 4,828,543 A | 5/1989 | Weiss et al. | |
| 4,840,542 A | 6/1989 | Abbott | |
| 4,902,282 A | 2/1990 | Bellotti et al. | |
| 4,902,877 A | 2/1990 | Grasso et al. | |
| 4,923,681 A | 5/1990 | Cox et al. | |
| 4,927,411 A | 5/1990 | Pastrone et al. | |
| 4,950,134 A | 8/1990 | Bailey et al. | |
| 4,976,162 A | 12/1990 | Kamen | |
| 4,997,464 A | 3/1991 | Kopf | |
| 5,002,471 A | 3/1991 | Perlov | |
| 5,036,886 A | 8/1991 | Olsen et al. | |
| 5,061,236 A | 10/1991 | Sutherland et al. | |
| 5,079,410 A | 1/1992 | Payne et al. | |
| 5,088,515 A | 2/1992 | Kamen | |
| 5,097,402 A * | 3/1992 | Kriz et al. | 363/61 |
| 5,098,262 A | 3/1992 | Wecker et al. | |
| 5,100,380 A | 3/1992 | Epstein et al. | |
| 5,100,699 A | 3/1992 | Roeser | |
| 5,116,021 A | 5/1992 | Faust et al. | |
| 5,116,316 A | 5/1992 | Sertic et al. | |
| 5,146,713 A | 9/1992 | Grafius | |
| 5,151,019 A | 9/1992 | Danby et al. | |
| 5,167,837 A | 12/1992 | Snodgrass et al. | |
| 5,171,029 A | 12/1992 | Maxwell et al. | |
| 5,178,182 A | 1/1993 | Kamen | |
| 5,187,990 A | 2/1993 | Magnussen et al. | |
| 5,193,990 A | 3/1993 | Kamen et al. | |
| 5,211,201 A | 5/1993 | Kamen et al. | |
| 5,229,577 A | 7/1993 | Matsuura et al. | |
| 5,241,985 A | 9/1993 | Faust et al. | |
| 5,247,434 A | 9/1993 | Peterson et al. | |
| 5,250,027 A | 10/1993 | Lewis et al. | |
| 5,252,044 A | 10/1993 | Raines et al. | |
| 5,279,556 A | 1/1994 | Goi et al. | |
| 5,302,093 A | 4/1994 | Owens et al. | |
| 5,311,908 A | 5/1994 | Barone et al. | |
| 5,315,632 A | 5/1994 | Flynn et al. | |
| 5,324,422 A | 6/1994 | Colleran et al. | |
| 5,330,425 A | 7/1994 | Utterberg | |
| 5,350,357 A | 9/1994 | Kamen et al. | |
| 5,353,837 A | 10/1994 | Faust | |
| 5,354,967 A | 10/1994 | Barzilai et al. | |
| 5,395,351 A | 3/1995 | Munsch | |
| 5,421,208 A | 6/1995 | Packard et al. | |
| 5,421,823 A | 6/1995 | Kamen et al. | |
| 5,427,509 A | 6/1995 | Chapman et al. | |
| 5,431,626 A | 7/1995 | Bryant et al. | |
| 5,431,627 A | 7/1995 | Pastrone et al. | |
| 5,431,634 A | 7/1995 | Brown | |
| 5,438,510 A | 8/1995 | Bryant et al. | |
| 5,441,636 A | 8/1995 | Chevallet et al. | |
| 5,445,506 A | 8/1995 | Afflerbaugh et al. | |
| 5,447,286 A | 9/1995 | Kamen et al. | |
| 5,450,743 A | 9/1995 | Buote et al. | |
| 5,462,416 A | 10/1995 | Dennehey et al. | |
| 5,462,417 A | 10/1995 | Chapman | |
| 5,474,683 A | 12/1995 | Bryant et al. | |
| 5,478,211 A | 12/1995 | Dominiak et al. | |
| 5,480,294 A | 1/1996 | Di Perna et al. | |
| 5,482,438 A | 1/1996 | Anderson et al. | |
| 5,482,440 A | 1/1996 | Dennehey et al. | |
| 5,482,446 A | 1/1996 | Williamson et al. | |
| 5,483,149 A | 1/1996 | Barrett | |
| 5,484,239 A | 1/1996 | Chapman et al. | |
| 5,486,286 A | 1/1996 | Peterson et al. | |
| 5,514,069 A | 5/1996 | Brown et al. | |
| 5,514,102 A | 5/1996 | Winterer et al. | |
| 5,538,405 A | 7/1996 | Patno et al. | |
| 5,547,453 A | 8/1996 | Di Perna | |
| 5,551,850 A | 9/1996 | Williamson et al. | |
| 5,551,941 A | 9/1996 | Howell | |
| 5,551,942 A | 9/1996 | Brown et al. | |
| 5,554,013 A | 9/1996 | Owens et al. | |
| 5,570,716 A | 11/1996 | Kamen et al. | |
| 5,578,070 A | 11/1996 | Utterberg | |
| 5,596,236 A | 1/1997 | Lee et al. | |
| 5,609,572 A | 3/1997 | Lang | |
| 5,614,677 A | 3/1997 | Wamsiedler et al. | |
| 5,624,572 A | 4/1997 | Larson et al. | |
| 5,628,908 A | 5/1997 | Kamen et al. | |
| 5,630,710 A | 5/1997 | Tune et al. | |
| 5,634,896 A | 6/1997 | Bryant et al. | |
| 5,640,995 A | 6/1997 | Packard et al. | |
| 5,641,405 A | 6/1997 | Keshaviah et al. | |
| 5,641,892 A | 6/1997 | Larkins et al. | |
| 5,643,205 A | 7/1997 | Utterberg | |
| 5,658,133 A | 8/1997 | Anderson et al. | |
| 5,690,602 A | 11/1997 | Brown et al. | |
| 5,713,865 A | 2/1998 | Manning et al. | |
| 5,713,888 A | 2/1998 | Neuenfeldt et al. | |
| 5,741,125 A | 4/1998 | Neftel et al. | |
| 5,746,708 A | 5/1998 | Giesler et al. | |
| 5,755,683 A | 5/1998 | Houle et al. | |
| 5,764,034 A | 6/1998 | Bowman et al. | |
| 5,771,914 A | 6/1998 | Ling et al. | |
| 5,772,635 A | 6/1998 | Dastur et al. | |
| 5,772,637 A | 6/1998 | Heinzmann et al. | |
| 5,782,805 A | 7/1998 | Meinzer et al. | |
| 5,799,207 A | 8/1998 | Wang et al. | |
| 5,816,779 A | 10/1998 | Lawless et al. | |
| 5,840,151 A | 11/1998 | Munsch | |
| 5,842,841 A | 12/1998 | Danby et al. | |
| 5,843,035 A | 12/1998 | Bowman et al. | |
| 5,868,696 A | 2/1999 | Giesler et al. | |
| 5,873,853 A | 2/1999 | Keilman et al. | |
| 5,906,598 A | 5/1999 | Giesler et al. | |

(56) References Cited

U.S. PATENT DOCUMENTS

| | | | |
|---|---|---|---|
| 5,908,571 A * | 6/1999 | Scott | 219/457.1 |
| 5,935,099 A | 8/1999 | Peterson et al. | |
| 5,938,634 A | 8/1999 | Packard | |
| 5,989,423 A | 11/1999 | Kamen | |
| 5,993,174 A | 11/1999 | Konishi | |
| 5,996,634 A | 12/1999 | Dennehey et al. | |
| 6,013,057 A | 1/2000 | Danby et al. | |
| 6,036,668 A | 3/2000 | Mathis | |
| 6,036,680 A | 3/2000 | Horne et al. | |
| 6,041,801 A | 3/2000 | Gray et al. | |
| 6,047,108 A | 4/2000 | Sword et al. | |
| 6,065,941 A | 5/2000 | Gray et al. | |
| 6,068,612 A | 5/2000 | Bowman et al. | |
| 6,074,359 A | 6/2000 | Keshaviah et al. | |
| 6,099,492 A | 8/2000 | Le Boeuf | |
| 6,111,230 A | 8/2000 | Cao et al. | |
| 6,118,207 A | 9/2000 | Ormerod et al. | |
| 6,129,517 A | 10/2000 | Danby et al. | |
| 6,136,565 A | 10/2000 | Best et al. | |
| 6,154,605 A | 11/2000 | Aonuma | |
| 6,164,621 A | 12/2000 | Bouchard et al. | |
| 6,165,154 A | 12/2000 | Gray et al. | |
| 6,179,801 B1 | 1/2001 | Holmes et al. | |
| 6,184,356 B1 | 2/2001 | Anderson et al. | |
| 6,196,987 B1 | 3/2001 | Holmes et al. | |
| 6,200,287 B1 | 3/2001 | Keller et al. | |
| 6,208,107 B1 | 3/2001 | Maske et al. | |
| 6,220,295 B1 | 4/2001 | Bouchard et al. | |
| 6,223,130 B1 | 4/2001 | Gray et al. | |
| 6,227,807 B1 | 5/2001 | Chase | |
| 6,228,047 B1 | 5/2001 | Dadson | |
| 6,231,537 B1 | 5/2001 | Holmes et al. | |
| 6,234,989 B1 | 5/2001 | Brierton et al. | |
| 6,250,502 B1 | 6/2001 | Cote et al. | |
| 6,261,065 B1 | 7/2001 | Nayak et al. | |
| 6,267,242 B1 | 7/2001 | Nagata et al. | |
| 6,270,673 B1 | 8/2001 | Belt et al. | |
| 6,280,406 B1 | 8/2001 | Dolecek et al. | |
| 6,281,145 B1 | 8/2001 | Deguchi et al. | |
| 6,284,142 B1 | 9/2001 | Muller | |
| 6,285,155 B1 | 9/2001 | Maske et al. | |
| 6,294,094 B1 | 9/2001 | Muller et al. | |
| 6,296,450 B1 | 10/2001 | Westberg et al. | |
| 6,297,322 B1 | 10/2001 | Ding et al. | |
| 6,315,707 B1 | 11/2001 | Smith et al. | |
| 6,316,864 B1 | 11/2001 | Ormerod | |
| 6,322,488 B1 | 11/2001 | Westberg et al. | |
| 6,325,775 B1 | 12/2001 | Thom et al. | |
| 6,337,049 B1 | 1/2002 | Tamari | |
| 6,343,614 B1 | 2/2002 | Gray et al. | |
| 6,348,156 B1 | 2/2002 | Vishnoi et al. | |
| 6,361,518 B1 | 3/2002 | Brierton et al. | |
| 6,364,857 B1 | 4/2002 | Gray et al. | |
| 6,382,923 B1 | 5/2002 | Gray | |
| 6,383,158 B1 | 5/2002 | Utterberg | |
| 6,406,276 B1 | 6/2002 | Normand et al. | |
| 6,409,696 B1 | 6/2002 | Toavs et al. | |
| 6,416,293 B1 | 7/2002 | Bouchard et al. | |
| 6,419,822 B2 | 7/2002 | Muller et al. | |
| 6,455,676 B1 | 9/2002 | Weickert et al. | |
| 6,459,175 B1 | 10/2002 | Potega | |
| 6,471,855 B1 | 10/2002 | Odak et al. | |
| 6,481,980 B1 | 11/2002 | Vandlik et al. | |
| 6,489,896 B1 | 12/2002 | Platt et al. | |
| 6,491,656 B1 | 12/2002 | Morris et al. | |
| 6,497,674 B1 | 12/2002 | Steele et al. | |
| 6,497,676 B1 | 12/2002 | Childers et al. | |
| 6,503,062 B1 | 1/2003 | Gray et al. | |
| 6,514,225 B1 | 2/2003 | Utterberg et al. | |
| 6,519,569 B1 | 2/2003 | White et al. | |
| 6,520,747 B2 | 2/2003 | Gray et al. | |
| 6,524,231 B1 | 2/2003 | Westberg et al. | |
| 6,537,445 B2 | 3/2003 | Muller | |
| 6,542,761 B1 | 4/2003 | Jahn et al. | |
| 6,558,343 B1 | 5/2003 | Neftel | |
| 6,572,604 B1 | 6/2003 | Platt et al. | |
| 6,592,542 B2 | 7/2003 | Childers et al. | |
| 6,595,948 B2 | 7/2003 | Suzuki et al. | |
| 6,603,229 B1 | 8/2003 | Toye, IV | |
| 6,604,908 B1 | 8/2003 | Bryant et al. | |
| 6,614,008 B2 | 9/2003 | Tidrick | |
| 6,645,166 B2 | 11/2003 | Scheunert et al. | |
| 6,645,177 B1 | 11/2003 | Shearn | |
| 6,648,861 B2 | 11/2003 | Platt et al. | |
| 6,663,359 B2 | 12/2003 | Gray | |
| 6,670,323 B1 | 12/2003 | Lee et al. | |
| 6,695,803 B1 | 2/2004 | Robinson et al. | |
| 6,709,417 B1 | 3/2004 | Houle et al. | |
| 6,716,004 B2 | 4/2004 | Vandlik et al. | |
| 6,723,062 B1 | 4/2004 | Westberg et al. | |
| 6,725,726 B1 | 4/2004 | Adolfs et al. | |
| 6,726,656 B2 | 4/2004 | Kamen et al. | |
| 6,730,055 B2 | 5/2004 | Bainbridge et al. | |
| 6,743,201 B1 | 6/2004 | Doenig et al. | |
| 6,746,514 B2 | 6/2004 | Bedingfield et al. | |
| 6,749,403 B2 | 6/2004 | Bryant et al. | |
| 6,752,172 B2 | 6/2004 | Lauer | |
| 6,755,801 B2 | 6/2004 | Utterberg et al. | |
| 6,758,975 B2 | 7/2004 | Peabody et al. | |
| 6,759,007 B1 | 7/2004 | Westberg et al. | |
| 6,764,460 B2 | 7/2004 | Dolecek et al. | |
| 6,764,761 B2 | 7/2004 | Eu et al. | |
| 6,768,425 B2 | 7/2004 | Flaherty et al. | |
| 6,774,517 B2 | 8/2004 | Kowalski et al. | |
| 6,790,195 B2 | 9/2004 | Steele et al. | |
| 6,790,198 B1 | 9/2004 | White et al. | |
| 6,800,054 B2 | 10/2004 | Westberg et al. | |
| 6,808,369 B2 | 10/2004 | Gray et al. | |
| 6,814,547 B2 | 11/2004 | Childers et al. | |
| 6,821,432 B2 | 11/2004 | Metzner | |
| 6,828,125 B1 | 12/2004 | Hoffman et al. | |
| 6,846,161 B2 | 1/2005 | Kline et al. | |
| 6,852,090 B2 | 2/2005 | Burbank et al. | |
| 6,869,538 B2 | 3/2005 | Yu et al. | |
| 6,905,479 B1 | 6/2005 | Bouchard et al. | |
| 6,929,751 B2 | 8/2005 | Bowman et al. | |
| 6,939,111 B2 | 9/2005 | Huitt et al. | |
| 6,947,683 B2 | 9/2005 | Na | |
| 6,949,079 B1 | 9/2005 | Westberg et al. | |
| 6,953,323 B2 | 10/2005 | Childers et al. | |
| 6,969,373 B2 | 11/2005 | Schwartz et al. | |
| 6,984,218 B2 | 1/2006 | Nayak et al. | |
| 7,021,148 B2 | 4/2006 | Jensen et al. | |
| 7,033,539 B2 | 4/2006 | Krensky et al. | |
| 7,041,076 B1 | 5/2006 | Westberg et al. | |
| 7,044,432 B2 | 5/2006 | Beden et al. | |
| 7,049,406 B2 | 5/2006 | Weickert et al. | |
| 7,083,719 B2 | 8/2006 | Bowman et al. | |
| 7,087,036 B2 | 8/2006 | Busby et al. | |
| 7,107,837 B2 | 9/2006 | Lauman et al. | |
| 7,115,107 B2 | 10/2006 | Delnevo et al. | |
| 7,115,228 B2 | 10/2006 | Lundtveit et al. | |
| 7,147,613 B2 | 12/2006 | Burbank et al. | |
| 7,153,286 B2 | 12/2006 | Busby et al. | |
| 7,160,087 B2 | 1/2007 | Fathallah et al. | |
| 7,166,231 B2 | 1/2007 | Westberg et al. | |
| 7,175,606 B2 | 2/2007 | Bowman et al. | |
| 7,195,607 B2 | 3/2007 | Westberg et al. | |
| 7,211,560 B2 | 5/2007 | Looker et al. | |
| 7,232,435 B2 | 6/2007 | Hildebrand et al. | |
| 7,236,936 B2 | 6/2007 | White et al. | |
| 7,238,164 B2 | 7/2007 | Childers et al. | |
| 7,255,680 B1 | 8/2007 | Gharib | |
| 7,258,534 B2 | 8/2007 | Fathallah et al. | |
| 7,267,661 B2 | 9/2007 | Susi | |
| 7,338,472 B2 | 3/2008 | Shearn | |
| 7,345,025 B2 | 3/2008 | Symonds et al. | |
| 7,347,836 B2 | 3/2008 | Peterson et al. | |
| 7,390,311 B2 | 6/2008 | Hildebrand et al. | |
| 7,398,183 B2 | 7/2008 | Holland et al. | |
| 7,399,637 B2 | 7/2008 | Wright et al. | |
| 7,403,704 B2 | 7/2008 | Eccleston et al. | |
| 7,404,809 B2 | 7/2008 | Susi | |
| 7,410,475 B2 | 8/2008 | Krensky et al. | |

(56) References Cited

U.S. PATENT DOCUMENTS

| | | |
|---|---|---|
| 7,422,905 B2 | 9/2008 | Clague et al. |
| 7,454,314 B2 | 11/2008 | Holland et al. |
| 7,490,021 B2 | 2/2009 | Holland et al. |
| 7,500,962 B2 | 3/2009 | Childers et al. |
| 7,517,387 B2 | 4/2009 | Chevallet et al. |
| 7,553,295 B2 | 6/2009 | Susi |
| 7,556,616 B2 | 7/2009 | Fathallah et al. |
| 7,575,564 B2 | 8/2009 | Childers |
| 7,618,948 B2 | 11/2009 | Kaemmerer |
| 7,645,258 B2 | 1/2010 | White et al. |
| 7,648,627 B2 | 1/2010 | Beden et al. |
| 7,654,976 B2 | 2/2010 | Peterson et al. |
| 7,662,286 B2 | 2/2010 | Childers et al. |
| 7,699,966 B2 | 4/2010 | Qin et al. |
| 7,782,590 B2* | 8/2010 | Bedingfield et al. ......... 361/160 |
| 7,789,849 B2 | 9/2010 | Busby et al. |
| 7,815,595 B2 | 10/2010 | Busby |
| 8,160,433 B2* | 4/2012 | Bedingfield et al. ......... 392/315 |
| 8,331,819 B2* | 12/2012 | Fukuzawa et al. ............. 399/69 |
| 2001/0034502 A1 | 10/2001 | Moberg |
| 2001/0037763 A1 | 11/2001 | Deguchi et al. |
| 2002/0000793 A1 | 1/2002 | Hanaki |
| 2002/0045851 A1 | 4/2002 | Suzuki et al. |
| 2002/0062105 A1 | 5/2002 | Tanner et al. |
| 2002/0062109 A1 | 5/2002 | Lauer |
| 2002/0072718 A1 | 6/2002 | Brugger et al. |
| 2002/0107474 A1 | 8/2002 | Noack |
| 2002/0147423 A1 | 10/2002 | Burbank et al. |
| 2003/0018395 A1 | 1/2003 | Crnkovich et al. |
| 2003/0028144 A1 | 2/2003 | Duchon et al. |
| 2003/0029451 A1 | 2/2003 | Blair et al. |
| 2003/0042181 A1 | 3/2003 | Metzner |
| 2003/0085621 A1 | 5/2003 | Potega |
| 2003/0100882 A1 | 5/2003 | Beden et al. |
| 2003/0111457 A1 | 6/2003 | Tidrick |
| 2003/0136189 A1 | 7/2003 | Lauman et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0084647 A1 | 5/2004 | Beden et al. |
| 2004/0135078 A1 | 7/2004 | Mandro et al. |
| 2004/0156745 A1 | 8/2004 | Vandlik et al. |
| 2004/0195190 A1 | 10/2004 | Min et al. |
| 2004/0232137 A1* | 11/2004 | Cook et al. .................. 219/486 |
| 2004/0238416 A1 | 12/2004 | Burbank et al. |
| 2005/0054968 A1 | 3/2005 | Giannella |
| 2005/0080316 A1 | 4/2005 | Severns |
| 2005/0165354 A1 | 7/2005 | Schwartz et al. |
| 2005/0209563 A1 | 9/2005 | Hopping et al. |
| 2005/0230292 A1 | 10/2005 | Beden et al. |
| 2005/0286189 A1 | 12/2005 | Rhodes |
| 2006/0079826 A1 | 4/2006 | Beden et al. |
| 2006/0195064 A1 | 8/2006 | Plahey et al. |
| 2007/0112297 A1 | 5/2007 | Plahey et al. |
| 2007/0149913 A1 | 6/2007 | Busby et al. |
| 2007/0193940 A1 | 8/2007 | Duchamp et al. |
| 2007/0213651 A1 | 9/2007 | Busby et al. |
| 2007/0213653 A1 | 9/2007 | Childers et al. |
| 2007/0213654 A1 | 9/2007 | Lundtveit et al. |
| 2007/0269340 A1 | 11/2007 | Dannenmaier et al. |
| 2008/0033346 A1 | 2/2008 | Childers et al. |
| 2008/0058712 A1 | 3/2008 | Plahey |
| 2008/0077068 A1 | 3/2008 | Orr |
| 2008/0208103 A1 | 8/2008 | Demers et al. |
| 2009/0004033 A1 | 1/2009 | Demers et al. |
| 2009/0312694 A1 | 12/2009 | Bedingfield et al. |
| 2011/0040242 A1 | 2/2011 | Fallon et al. |
| 2012/0168426 A1 | 7/2012 | Hedmann et al. |

FOREIGN PATENT DOCUMENTS

| | | |
|---|---|---|
| DE | 4026138 | 1/1997 |
| DE | 19837667 | 3/2000 |
| DE | 10042324 | 2/2002 |
| DE | 10046651 | 4/2002 |
| DE | 10053441 | 5/2002 |
| DE | 10157924 | 5/2002 |
| DE | 10143137 | 4/2003 |
| EP | 0380140 A2 | 8/1990 |
| EP | 0728509 | 8/1996 |
| EP | 0804049 A2 | 10/1997 |
| EP | 0856321 | 8/1998 |
| EP | 0947814 B2 | 10/1999 |
| EP | 0956876 A1 | 11/1999 |
| EP | 1529545 | 5/2005 |
| GB | 725230 | 3/1955 |
| GB | 2181311 | 5/1987 |
| GB | 2293098 | 3/1996 |
| JP | 561164430 | 7/1986 |
| JP | 04191755 | 7/1992 |
| JP | 06002650 | 1/1994 |
| JP | 06154314 | 6/1994 |
| JP | H071469 | 1/1995 |
| JP | H07163114 | 6/1995 |
| JP | 07046804 | 10/1995 |
| JP | 9225022 A | 9/1997 |
| JP | 1085323 | 4/1998 |
| JP | 10108425 | 4/1998 |
| JP | 11347115 | 12/1999 |
| JP | 2000005072 A | 1/2000 |
| JP | 2000070358 | 3/2000 |
| JP | 2004030988 A | 1/2004 |
| JP | 2004248439 A | 9/2004 |
| JP | 2004266970 A | 9/2004 |
| JP | 3622513 B2 | 12/2004 |
| JP | 2006043466 A | 2/2006 |
| WO | 8402473 | 7/1984 |
| WO | 8601115 | 2/1986 |
| WO | 9716214 | 5/1997 |
| WO | 9737703 | 10/1997 |
| WO | 9822165 | 5/1998 |
| WO | 0023140 | 4/2000 |
| WO | 0033898 | 6/2000 |
| WO | 0117605 | 3/2001 |
| WO | 0225225 | 3/2002 |
| WO | 03099355 | 12/2003 |
| WO | 200589832 | 9/2005 |
| WO | WO2009105413 A2 | 8/2009 |
| WO | WO2012076176 A1 | 6/2012 |

OTHER PUBLICATIONS

Gambro®, Prisma® HF 1000, "For Increased Filtration Capacity", Gambro Renal Products, Inc., Lakewood, CO, pp. 1-2; © Aug. 2001.

Gambro®, "DEHP-Free Cartridge Blood Sets," © Nov. 2004, Gambro, Inc., Lakewood, CO, pp. 1-4; Nov. 2004.

Gambro®, "Prisma® M60 and M100 Pre-Pump Infusion Sets—Introducing: The unique solution that enables Physicians to choose a predilution method that meets the needs of their patients", Gambro Inc., Lakewood, CO, 4 pp; © 2004.

Gambro®, "Prismaflex™ Anticipating Critical Care needs and taking our innovative response to new heights," Gambro Inc., Lakewood, CO, 8 pp.; © 2004.

Glenn Avolio, "Principles of Rotary Optical Encoders," Sensors Journal of Machine Perception, vol. 10,1 No. 4, pp. 10-18, 1993.

(56) References Cited

OTHER PUBLICATIONS

Liberty Cycler User's Guide, pp. 1-174, 2008.
Manns, Markus et al, "The acu-men: A new device for continuous renal replacement therapy in acute renal failure," Kidney International, vol. 54, pp. 268-274, 1998.
Newton IQ Cycler Operator Manual, Part No. 470203 Rev. F, 2000-2006.
Operator's Instructions, Fresenius 90/2 Peritoneal Therapy Cycler, Part No. 470016 Rev. B, 1991.
Operator's Manual, Serena, Program Version 3.xx—English; Apr. 2002.
Sleep Safe Technical Manual, Part No. 677 807 1; Aug. 2000.
Revocation Claim filed by Baxter Healthcare Corporation against Fresenius Medical Care Holdings, Inc., dated Jul. 19, 2013; Particulars of Claim; Grounds of Invalidity; Annex A to the Grounds of Invalidity (Sales Order Detail No. 42113 allegedly related to sale of Baxter "HomeChoice Neptune" dual voltage peritoneal dialysis machine serial No. 5C8301 on or around Aug. 15, 1999 to Great Eastern Healthcare Limited); Annex B to the Grounds of Invalidity (Baxter Design Review dated Jun. 24, 1998); Annex C to the Grounds of Invalidity (Drawings allegedly related to Nullity Complaint filed by Baxter Healthcare SA against Fresenius Medical Care Holdings, Inc., dated Sep. 30, 2013 for German patent No. DE 60 2007 015 026.4, 66 pp. (English translation provided, 58 pp.) includes cited documents: N2, "Excerpt from the register of the German Patent and Trade Mark Office regarding the patent in suit," Jul. 25, 2013, 4 pp.; N3, "Feature analysis of claim 1 of the patent in suit," 1 pp.; K1a, "Home Choice, HomeChoice Pro Automated PD Systems: At Home Patient Guide," Baxter, 1994, 138 pp.; K1b Product Family: Peritoneal.
International Preliminary Examination Report issued in the parallel PCT application No. PCT/EP2011/006188, issued Jun. 12, 2013, 44 pages.
First Office Action issued in a parallel Chinese Application No. 201180059638.7, issued Feb. 2, 2015, 23 pages.
Second Office Action issued in a parallel Chinese Application No. 201180059638.7, issued Aug. 31, 2015, 31 pages.

\* cited by examiner

# MEDICAL DEVICE HEATERS AND METHODS

CROSS-REFERENCE TO RELATED APPLICATIONS

This application is a continuation of U.S. application Ser. No. 13/315,240, filed Dec. 8, 2011, which claims the benefit under 35 U.S.C. §119(e) of U.S. Provisional Patent Application No. 61/421,332, filed on Dec 9, 2010, which is incorporated by reference, and claims priority under 35 U.S.C. §119(a) to German Patent Application No. 10 2010 053 973.2, filed on Dec. 9, 2010.

TECHNICAL FIELD

The present invention relates to medical device heaters and methods.

BACKGROUND

In dialysis machines, heating of dialysis fluid is usually realized as an ohmic heating element to which a heating control applies mains voltage to switch the heating element on or to disconnect the heating element from the mains voltage in order to switch it off.

The heating power can be set and adapted to the different rated voltages to split the heater into a plurality of heating elements or to control the heating elements via a phase angle control. Phase angle controls are, however, complicated and moreover have problems with electromagnetic irradiation. There is moreover a substantial power loss in the electronic system. The previously known division into a plurality of heating elements furthermore has the disadvantage that the devices have to be switched differently at different rated voltages of the mains power in order not to reach any unpermittedly high power consumption.

SUMMARY

In one aspect of the invention, a medical device (e.g. a dialysis machine) has a heater with at least one heating element as well as a heating control unit. The heating control unit applies mains voltage to the heating element. The heating control unit in this respect includes a monitoring arrangement and a switching arrangement. The monitoring arrangement can recognize the zero crossings of the mains voltage, and the switching arrangement can switch the at least one heating element on or off in the zero crossing.

The heating control unit controls the power of the heating via the switching on and off of one or more half cycles of the mains voltage.

Individual half cycles of the mains voltage can be switched on or off in this process. However, pulse packets can naturally also be connected with a plurality of half cycles or periods of the mains voltage. In this respect, the power is set via the ratio of the number of the half cycles with a switched on heating element to the number of the half cycles with a switched off heating element. In this respect, the irradiation, the number of components, and the power loss in the electronic system is considerably reduced with respect to a phase angle control.

In an advantageous embodiment of the present invention, the monitoring arrangement detects the level of the mains voltage, and the heating control unit adapts the control of the at least one heating element to the detected level of the mains power supply. The medical device (e.g. dialysis machine) can be operated at different rated voltages of the mains voltage. The control of the power of the heating via the switching on and off of one or more half cycles of the mains voltage in particular allows an operation at different rated voltages of the mains power supply and/or allows an adaptation to fluctuating voltage levels of the mains power supply. The same maximum power of the heating at different mains AC voltages can in particular thus be provided. In this respect, the ratio of the number of the half cycles with a switched on heating element to the number of the half cycles with a switched off heating element is adapted to the detected level of the mains power supply, so that in each case the same maximum power of the heating is available independently of the level of the mains power supply.

The medical device (e.g. dialysis machine) can furthermore have at least two heating elements which can be switched on and off independently of one another by the switching arrangement. The division into two heating elements in this respect permits an even more flexible control of the power of the heating.

In this respect, with regard to the above-described control of the power of the heating via the number of the half cycles with a switched on heating element or with a switched off heating element, the number of the half cycles at which the first heating element is switched on and the number of half cycles at which the second heating element is switched on are advantageously added together, optionally while taking account of a factor for considering different rated powers of the two heating elements. The same applies to the number of the half cycles with a respective switched off first or second heating element.

In this respect, the heating control unit advantageously has a first operating mode in which the two heating elements are operated partially or fully synchronously. The two heating elements in this respect in particular have rated voltage half cycles applied synchronously in part or in full. A correspondingly higher power can also be achieved with a low supply voltage due to the synchronous operation of the two heating elements. In this respect, both heating elements can be switched off synchronously for a corresponding number of half cycles. Alternatively, however, it is also conceivable only to switch off one of the two heating elements in each case to reduce the power.

In some embodiments, the heating control unit has a second operating mode in which the at least two heating elements can be operated alternately. The two heating elements in this respect have a specific number of mains voltage half cycles applied alternately. In this second operating mode, for all mains voltage half-cycles in which the first heating element is switched on, the second heating element is switched off and vice versa. With this alternating operation, both heating elements can naturally also be switched off. The alternating operation of the two heating elements, in particular the operation of the two heating elements with one respective half cycle, makes it possible to maintain the amperage and/or power in a permitted range even at high supply voltages. The two heating elements are in this respect operated alternately with sequential half cycles.

In some embodiments the heating control unit selects the first or second operating mode in dependence on the detected level of the mains power supply. It can thus be ensured that the same maximum heating power is provided despite different rated voltages of the mains power supply. Currents which would overload the mains power supply and/or the heating elements can furthermore be avoided by the second operating mode, even at high rated voltages.

The heating control unit advantageously selects the first operating mode on detection of a mains AC voltage which is in a first, lower voltage range and the second operating mode on detection of a mains AC voltage in a second, higher voltage range. The first, lower region in this respect advantageously includes at least one mains AC voltage between 100 V and 120 V, (e.g., 100 V, 110 V or 120 V). The second higher range advantageously includes at least one mains AC voltage between 230 V and 250 V (e.g., 230 V or 240 V). In some embodiments, the first range includes the range between 90 V and 110 V. The first range can alternatively include the range between 80 V and 130 V or between 80 V and 160 V. The second range can advantageously include the range between 220 V and 240 V. The second range can alternatively include the range between 180 V and 250 V or between 160 V and 250 V.

In an operation in the first and/or second operating modes, the ratio of the number of the half cycles with a switched on heating element to the number of the half cycles with a switched off heating element is advantageously set in dependence on the level of the detected mains AC voltage. With a mains AC voltage which lies within the respective voltage range in which an operation takes place in the first and/or second operating modes, the maximum power of the heating can be kept constant and/or a desired power can be set.

The medical device can in this respect be operated in the first operating mode so that the two heating elements for setting the power are not acted on by all mains voltage half cycles, but are rather switched on and off synchronously or alternately for one or more mains voltage half cycles.

In the second operating mode, not every half cycle is switched either to the one or to the other heating element, but a corresponding number of half cycles is not switched to any of the heating elements to reduce the power. The number of mains voltage half cycles which can act on the heating elements can be changed accordingly depending on the level of the mains AC voltage.

The above described devices and methods can also be used with more than two heating elements. For the example, the above described devices and methods could be implemented with three or four heating elements, where the three or four heating elements each alternately have half cycles applied in the second operating mode, so that a half cycle is always as a maximum switched to one of the heating elements. The alternate operation can in this respect take place, for example, in that one or more half cycles are sequentially switched to the individual heating elements. The heating resistance of each individual heating element can hereby be increased and thus the maximum power consumption correspondingly reduced at a high mains voltage. At a low voltage, the heating elements can then be operated in parallel in the first operating mode. More than four heating elements are naturally also conceivable in this respect.

In the above-described embodiments, the power of the heating was adapted to different levels of the mains power supply via the switching on and off of one or more half cycles of the mains voltage. The maximum power of the heating can thus be kept the same for different mains voltages. In addition, the occurrence of unpermittedly high currents can be avoided.

The devices and methods described herein can, however, also be used to set the power of the heating to a value below the maximum power for purposes of temperature regulation. The present invention can, for example, be used to set the heating to a value between 0 and 10% of the maximum power. The currently output power can also here be set by the ratio of the number of the half cycles with a switched on heating element to the number of the half cycles with a switched off heating element.

The medical device in this respect advantageously includes a temperature sensor, wherein the ratio of the number of the half cycles with a switched on heating element to the number of the half cycles with a switched off heating element can be set in dependence on a signal of the temperature sensor.

Such a temperature regulation can in this respect also be used independently of the adaptation of the power of the heating to different mains voltages, in particular also with those devices which can only be used with a single mains voltage. Such a temperature regulation is, however, advantageously combined with an adaptation to the operating voltage of the mains power supply.

In some embodiments, the heating control unit generates a control signal on the basis of the signal of the temperature sensor which is superimposed on the control signals for adapting the power to the detected level of the mains power supply. Different embodiments are conceivable for such a superimposition.

In some embodiments, an envelope signal with a longer switching period in comparison with the mains voltage period can be generated using the signal of the temperature sensor. The envelope signal can be superimposed on the adaptation of the power to the detected level of the mains power supply working at one or more mains voltage half cycles. Alternatively, the ratio of the number of the half cycles with a switched on heating element to the number of the half cycles with a switched off heating element can be set directly smoothly in time in dependence on the signal of the temperature sensor and of the detected level of the mains power supply.

In certain embodiments, one or more half cycles of the mains voltage are switched on and off. For example, individual mains voltage half cycles can be switched on and off. However, pulse packets of a plurality of half cycles of the mains voltage can also be switched on and off. For example, pulse packets of 1 to 100 mains voltage half cycles (e.g., 1 to 10 mains voltage half cycles) can be used.

The heating element is in this respect relatively slow in its reaction so that the temperature of the heating element does not rise and fall in a relevant manner with the switching on and off of the half cycles on the use of a plurality of half cycles of the mains voltage, but rather is only determined via the mean ratio of the number of the half cycles switched on and off. To achieve a setting of the power which is as fine-grained as possible over a large power range and/or a large range of mains DC voltages, the smallest number of switchable half cycles used for the control are typically, kept relatively low (e.g., at 1 to 5 half cycles, at 1 to 3 half cycles).

The ratio of the number of the half cycles with a switched on heating element to the number of the half cycles with a switched off heating element is in this respect advantageously determined for a specific time period or a specific number of half cycles and is used for the control. A typical time period in this respect can lie, for example, between 0.1 and 20 seconds (e.g., between 0.5 and 5 seconds).

The heating control unit can switch the respective next half cycles on or off at any time so that the ratio remains at a desired value within the time period used for the determination.

It is equally conceivable to redetermine the ratio required for the provision of the desired power of the number of the half cycles with a switched on heating element to the number of the half cycles with a switched off heating element after a fixed time period or after a fixed number of half cycles and then to carry out a corresponding control in the following time period or in the following fixed number of the half cycles. A typical time period can in this respect lie between 0.1 and 20 seconds (e.g., between 0.5 and 5 seconds). In this respect, the ratio is recalculated on the basis of the measured mains AC voltage and of the desired power.

The devices and methods described herein can be used in a dialysis machine wherein the heater is used for heating a medical liquid, such as dialysate or blood. In some embodiments, the medical device is a peritoneal dialyzer having a heater for heating dialysate. The devices and methods described can equally be used in infusion devices, in particular for heating an infusion solution.

The devices and methods can be used with any desired embodiments of dialysis machine heaters, including throughflow heaters, heating bag heaters, and heaters for heating a presentation or supply bag.

A temperature sensor which directly measures the temperature of the heating element can be used as a temperature sensor for regulating the temperature. Alternatively or additionally, a temperature sensor can also be used to determine the temperature of the medium to be heated, such as the temperature of the dialysate used in a peritoneal dialysis device.

In addition to the medical device with a heater, certain embodiments include a heating control unit for a medical device such as was described above. Such a heating control unit in this respect has the advantages such as were already described above.

In another aspect, a method for operating a medical device having a heater with at least one heating element or for operating a heating control unit for such a device includes detecting the zero crossings of the mains voltage and switching the at least one heating element on and off in the zero crossing, wherein the power of the heating is controlled via the number of the half cycles of the mains voltage with a switched on heating element.

The method advantageously takes place in this respect as was represented in more detail above with respect to the medical device. In this respect, the method can be a method for operating a medical device or a heating control unit of the type described above.

The heating control units described herein can improve the heating methods of medical devices by providing simple and effective heating for such medical devices.

The details of one or more embodiments of the invention are set forth in the accompanying drawings and the description below. Other aspects, features, and advantages will be apparent from the description and drawings, and from the claims.

DETAILED DESCRIPTION

The function of a dialysis machine in which the heating devices and methods described herein can be used will first be described generally. The dialysis machine to be described is a peritoneal dialysis machine. The components described below can, however, also be used in the same manner or in a similar manner for a hemodialysis machine.

Peritoneal dialysis is a variant of artificial hemodialysis in which the peritoneum of the patient which has a good blood supply is used as a filter membrane natural to the body. Dialysate is introduced into the abdominal cavity via a catheter for this purpose. In accordance with the principle of osmosis, urea components of the blood diffuse through the peritoneum into the dialysate present in the abdominal cavity. After a dwell time, the dialysate with the urea components is drained from the abdominal cavity.

In automatic peritoneal dialysis, a dialysis machine controls and monitors the introduction of the fresh dialysate into the abdominal cavity and the draining of the consumed dialysate (also referred to as spent dialysate). Such a dialysis machine, also called a cycler, usually fills and drains the abdominal cavity several times overnight, while the patient is asleep.

Figure 1A:
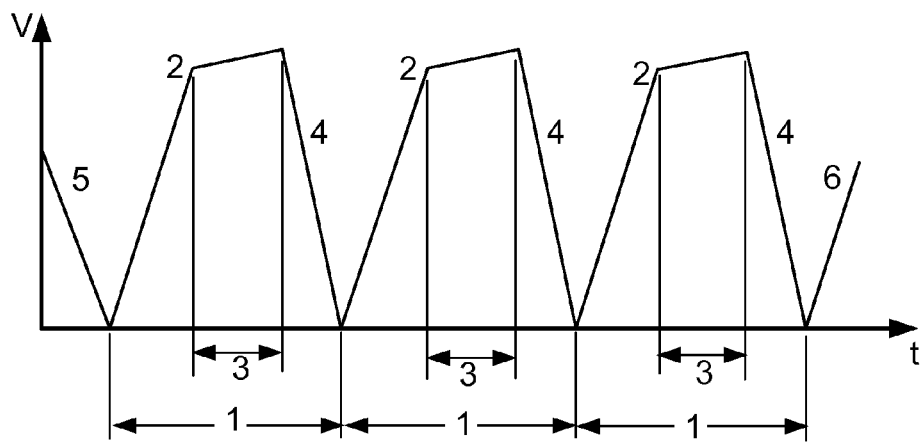
FIGS. 1a-1c illustrate three diagrams which show typical developments of an automatic peritoneal dialysis treatment.
Figure 1B:
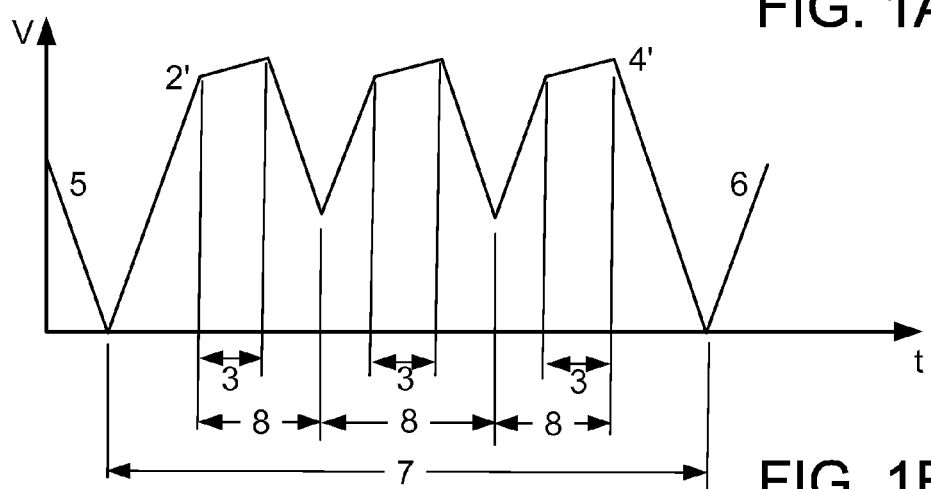
Figure 1C:
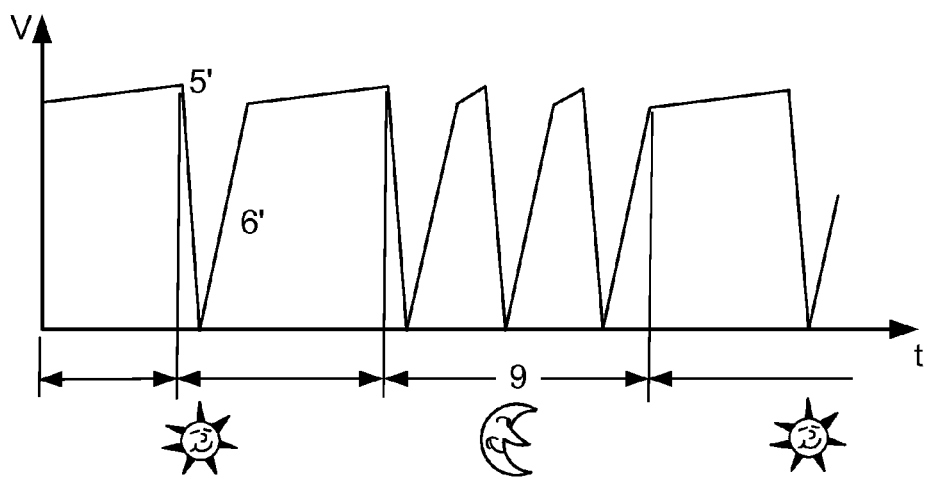

FIGS. 1a to 1c show three different procedures that are carried out by a dialysis machine. One or more of these procedures is usually stored in the controller of the dialysis machine. It is usually possible in this respect to adapt the stored procedures to the patient.

In FIGS. 1a to 1c, the dialysate quantity V respectively present in the patient's abdominal cavity is shown over the time t. In this respect, FIG. 1a shows the development of a normal automatic peritoneal dialysis treatment overnight. At the start of the treatment, an initial outflow or drain 5 occurs during which dialysate which was left in the abdominal cavity of the patient during the day is removed. A plurality of treatment cycles 1 then takes place. In FIG. 1a, three sequential treatment cycles 1 take place. Each treatment cycle comprises an inflow or fill phase 2, a dwell phase 3 and an outflow or drain phase 4. In this respect, a specific volume of fresh dialysate fluid is introduced into the patient's abdominal cavity during the inflow phase 2. The maximum permitted dialysate quantity in this respect amounts to between approximately 1.5 and 3 L depending on the patient. The fresh dialysate now remains in the abdominal cavity for a specific dwell time 3. The dwell phase in this respect typically lasts some hours. The consumed or spent dialysate is then removed from the abdominal cavity again in the outflow phase 4. A new treatment cycle then starts. The treatment is concluded with a last inflow 6 by which a specific quantity of fresh dialysate is introduced into the patient's abdominal cavity. It then remains in the patient's abdominal cavity throughout the day.

The individual treatment cycles 1 which take place overnight are in this respect automatically controlled by the controller of the dialysis machine. The initial outflow and the last inflow can likewise be controlled automatically by the dialysis machine. Alternatively, they can be activated manually by an operator or by the patient.

A so-called tidal treatment is shown in FIG. 1b. This also starts with an initial outflow 5 and ends with a last inflow 6. A base cycle 7 is also provided which is divided into a plurality of tidal cycles 8. In this respect, a base inflow phase 2' is initially provided. After the dwell time 3, however, the complete dialysate volume is not drained from the abdominal cavity, but rather only a certain portion of the dialysate present in the abdominal cavity is drained. This is then replaced by a corresponding volume of fresh dialysate. After a further dwell cycle, a further tidal removal can take place in which only a portion the total dialysate present in the abdomen is removed. At the end of the base cycle 7, a base outflow phase 4' takes place in which the total dialysate is removed. Only one base cycle 1 is shown in FIG. 1b. Alternatively, however, a plurality of base cycles can also be provided.

The course of a peritoneal dialysis treatment with a so-called peritoneal dialysis ("PD") plus treatment is shown in FIG. 1c. In this respect, a conventional peritoneal dialysis treatment takes place during the night 9 and can, for example, e.g. be carried out in accordance with FIG. 1a or 1b. An additional PD plus treatment is, however, also provided during the day in which the consumed dialysate is removed in an outflow phase 5' and is replaced by fresh dialysate in an inflow phase 6'. In the PD plus treatment, a normal night-time peritoneal dialysis treatment is combined with one or more additional treatment cycles during the day. The course of the night-time treatment is in this respect carried out as customary automatically by the dialysis machine. The treatment cycles during the day are likewise carried out and monitored via the machine.

Figure 2:
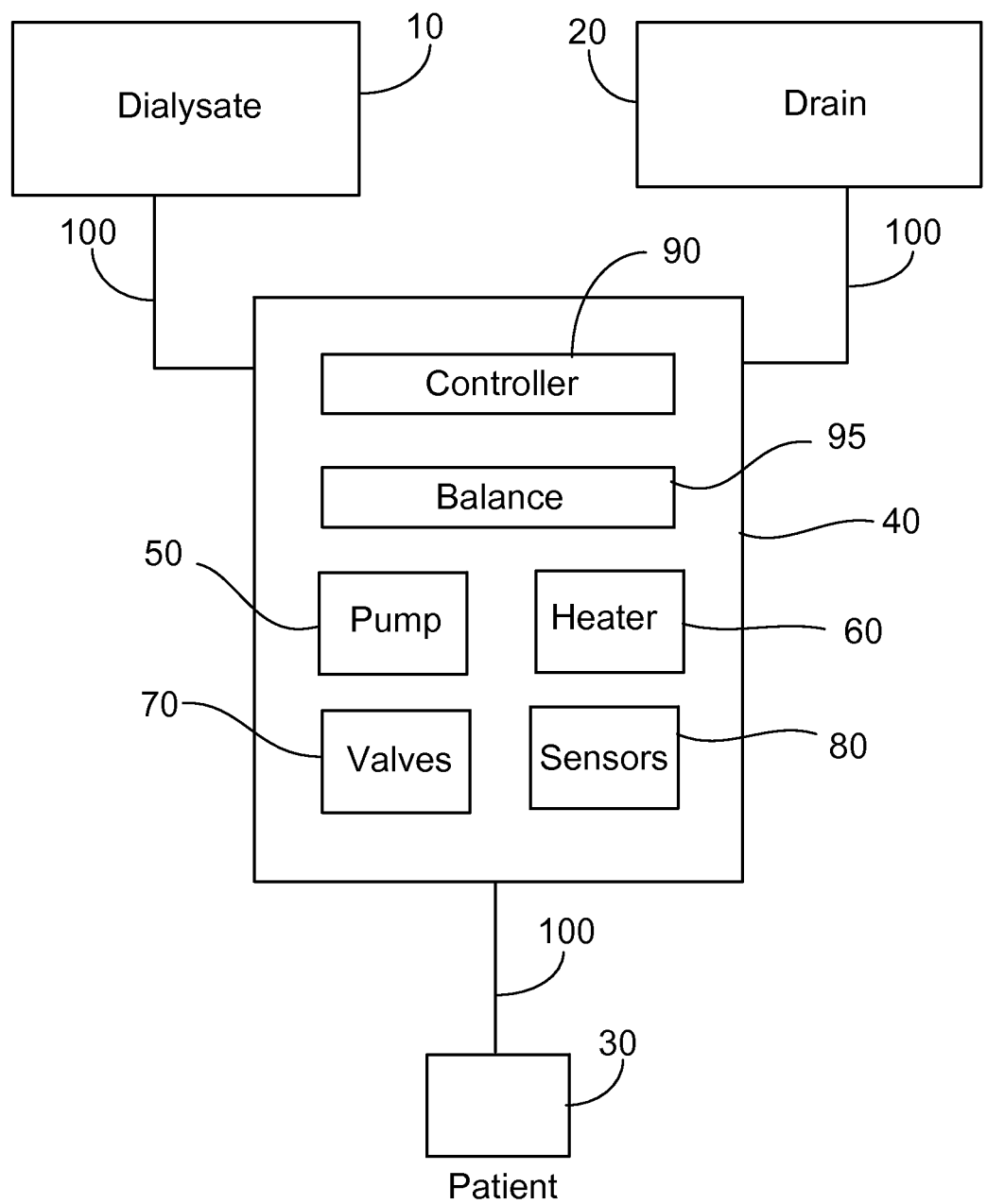
FIG. 2 is a schematic diagram of a peritoneal dialysis system.

The design of a typical peritoneal dialysis system is shown schematically in FIG. 2. The peritoneal dialysis system in this respect includes a container 10 with fresh dialysate and an outflow (e.g., a drain bag) 20 for used dialysate. A connector 30 is furthermore provided which can be connected to a catheter of the patient either to introduce fresh dialysate into the abdominal cavity of the patient or to remove consumed dialysate from the abdominal cavity. The container 10 with fresh dialysate, the drain bag 20 for used dialysate and the connector 30 to the patient are in this respect connected to one another via fluid paths 100 and form the fluid system of the peritoneal dialysis system.

A dialysis machine 40, also called a cycler, is provided for the carrying out of the peritoneal dialysis treatment. The dialysis machine 40 in this respect includes the following main components:

A pump 50 which is used for the transport of the fluids. The pump 50 in this respect conveys the fresh dialysate from the container 10 to the connector 30. The pump 50 can furthermore transport the consumed dialysate from the connector 30 to the drain bag 20.

Valves 70 which are used for the control of the fluid flows. The valves 70 open and close the fluid paths 100 in order to establish the corresponding fluid connections between the container 10, the connector 30 and the drain bag 20.

A heater 60 which brings the fresh dialysate to a temperature of approximately 37° C. before it is supplied to the patient. Since relatively large quantities of dialysate are supplied directly into the abdominal cavity of the patient in peritoneal dialysis, the heater 60 is used to maintain the body temperature of the patient within a desired range and to avoid an unpleasant feeling caused by dialysate which is too cold.

Sensors 80 via which the proper procedure of the treatment can be monitored and/or controlled. Temperature sensors can in particular be used in this respect. Pressure sensors can furthermore optionally be used.

The above-noted components of the dialysis machine 40 are controlled via a controller 90. In this respect, the controller 90 controls the pump 50, the heater 60 and the valves 70 on the basis of the data of the sensors 80. The controller 90 provides the automatic procedure of the peritoneal dialysis. The controller 90 includes a balance 95 which balances the fluid quantities supplied to and removed from the patient. The balance prevents the patient from being given too much fluid or having too much fluid removed.

The balance 95 can take place solely on the basis of the control data and/or the sensor data for the pump 50. Alternatively, the balance can also take place via separately provided balancing chambers. It is equally possible to use scales for the balancing. Such scales, for example, weigh the weight of the container 10 with fresh dialysate and/or the container 20 with used dialysate.

Since the dialysate is dispensed to the patient directly into the abdominal cavity in peritoneal analysis, extreme sterility must be observed. The fluid paths or the fluid system which come into contact with the fresh dialysate and/or the used dialysate are therefore usually designed as disposable parts. The fluid paths or the fluid system are in this respect typically designed as plastic parts. They can thus be supplied in a sterile outer packaging and only unpacked briefly before the treatment.

Figure 3:
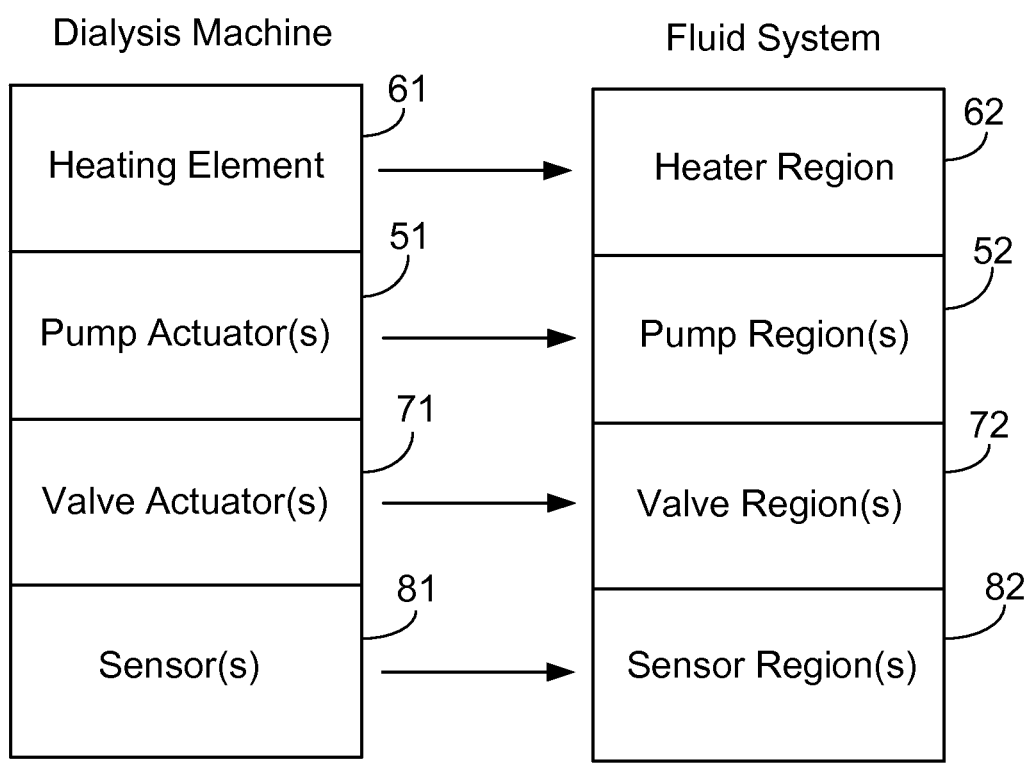
FIG. 3 is a schematic diagram of the division of the peritoneal dialysis system into a dialysis machine and a fluid system.

In order to enable a control of the peritoneal dialysis by the dialysis machine 40, the fluid system can be coupled to the dialysis machine 40. In this respect, it is shown schematically in FIG. 3 how individual elements of the dialysis machine 40 are coupled to corresponding regions of the fluid system.

The dialysis machine 40 in this respect has a heating element 61 to be coupled to a corresponding heating region 62 of the fluid system. The coupling in this respect enables the transfer of thermal energy from the heating element 61 to the dialysate present in the heating region 62.

The dialysis machine 40 also has one or more pump actuators 51 which are each coupled to a corresponding pump region 52 of the fluid system. The pump actuators 51 in this respect generate a pump force which is transferred to the pump region 52. The liquid present in the pump region 52 can hereby be moved along the fluid paths.

The dialysis machine also has one or more valve actuators 71. They generate a closing movement which is transferred to corresponding valve regions 72 of the fluid paths. The valve regions 72 of the fluid paths can hereby be correspondingly closed or opened.

The dialysis machine also has one or more sensors 81. They are each coupled to a corresponding sensor region 82 of the fluid system. The sensors 81 can hereby measure specific properties of the dialysate. The temperature of the dialysate can in particular be measured hereby. Provision can furthermore be made that the pressure in the fluid system is determined.

The dialysis machine optionally has further actuators and/or sensors which are not coupled to the fluid paths.

The individual components of a peritoneal dialysis system are now described in more detail in the following with reference to embodiments.

1. Fluid System 1.1 Dialysis Container

Fresh dialysate is usually provided in plastic bags. Such plastic bags usually have two layers of plastic film which are welded to one another in a marginal or peripheral region and thus form a container which is filled with fresh dialysate. A hose element is usually welded to this container by which the dialysate can be removed from the bag. A connector is usually arranged at the hose element via which the dialysate container can be connected to the other fluid paths. The bag also usually has a cutout or eyelet at the side disposed opposite the hose by which the bag can be hung onto a hook by it. It can hereby be ensured that the dialysate flows out of the bag without problem.

The dialysate usually comprises a buffer, an osmotic agent and electrolytes. Bicarbonate can, for example, be used as the buffer in this respect. Glucose is usually used as the osmotic agent. Alternatively, glucose polymers or glucose polymer derivatives can also be used. The electrolytes usually include calcium and sodium.

The dialysate can be heat sterilized in this respect. This advantageously takes place after the dialysate has been filled into the bag. Both the dialysate and the bag are hereby heat sterilized. In this respect, the filled bag is usually first packed into an outer packaging, whereupon the total system is sterilized.

Since the finished dialysate solution can often not be heat sterilized or cannot be stored for a long time due to the ingredients, provision can be made to store individual components of the dialysate separately and only to combine them shortly before the treatment. A first individual solution in this respect usually includes the buffer, while a second individual solution includes glucose and electrolytes. Optionally, more than two individual solutions, and thus more than two regions, can also be provided in a bag. In this respect, a multi-chamber bag (e.g., a double-chamber bag), can be provided which has a plurality of separate regions for the storage of the individual solutions. These regions are separated by a connection element which can be opened mechanically to mix the individual solutions with one another. A so-called peel seam can, for example, be provided between the two regions of the bag and opens on the application of a specific pressure to at least one of the regions of the bag.

Since relatively large quantities of dialysate are consumed during a night-time peritoneal dialysis treatment, a plurality of dialysate containers are usually used during the treatment. They are connected to the fluid paths via corresponding connectors and can be used for the filling of the patient by a corresponding connection of the valves.

1.2 Outflow

For the disposal of the consumed dialysis fluid, it can either be led off immediately into the drainage system or first be collected in an outflow container. A bag (i.e., a drain bag) is usually likewise used as an outflow container in this respect. It is empty before the start of the treatment and can thus take up the consumed dialysate. The bag can then be correspondingly disposed of after the end of the treatment.

1.3 Cassette

As already initially described, the fluid system has a plurality of regions in which the dialysis machine has an effect on the fluid system. The fluid system is coupled to the dialysis machine for this purpose.

Cassettes are used to simplify the coupling of the fluid paths to the dialysis machine and the effect of the corresponding elements of the dialysis machine on the fluid paths. A plurality of regions in which the dialysis machine has an effect on the fluid paths are jointly arranged in such a cassette. For this purpose, a cassette usually has a rigid base of plastic into which chambers open to one side are introduced as fluid paths. These chambers are covered by a flexible plastic film which provides the coupling to the dialysis machine. The flexible plastic film is in this respect usually welded to the rigid base in a marginal or peripheral region. The cassette is pressed with a coupling surface of the dialysis machine so that the actuators and/or sensors of the dialysis machine come into contact with corresponding regions of the cassette.

The cassette also has connections for the connection of the dialysate container 10, the connector 30, of the drain bag 20.

A cassette in this respect usually includes at least one pump region and one or more valve regions. The liquid transport can thus be controlled by the fluid system via the cassette. The cassette can furthermore have sensor regions which enable a simple coupling of sensors of the dialysis machine to the fluid system. The cassette can optionally also have one or more heating regions which can be coupled to corresponding heating elements of the dialysis machine.

Figure 4A:
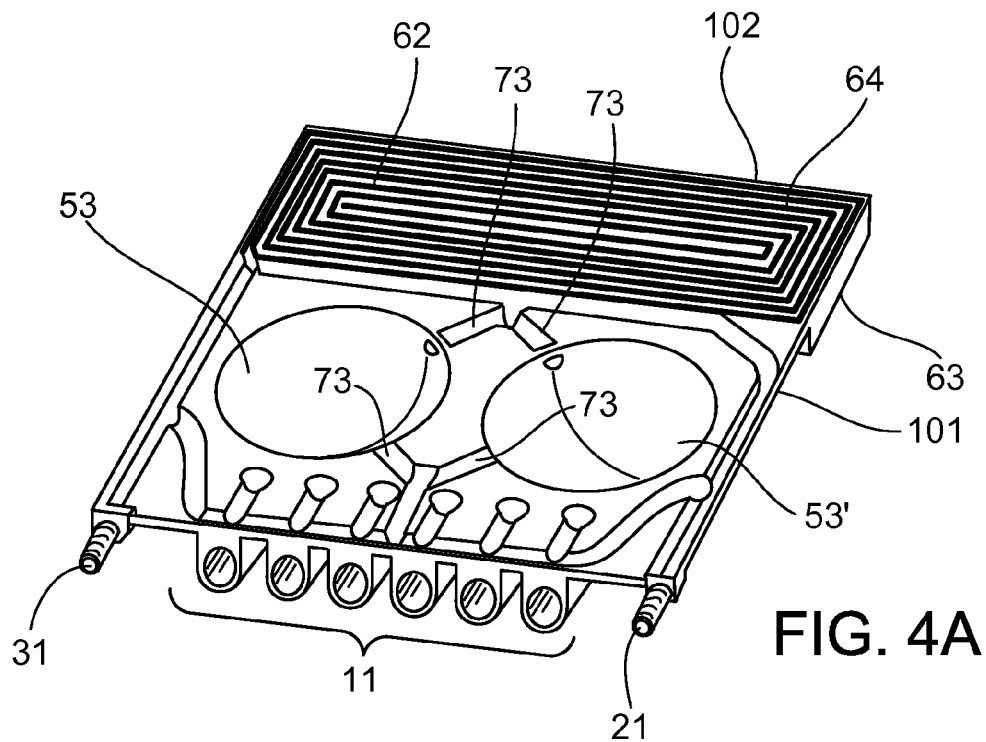
FIGS. 4a and 4b are perspective and plan views of a first embodiment of a cassette.
Figure 4B:
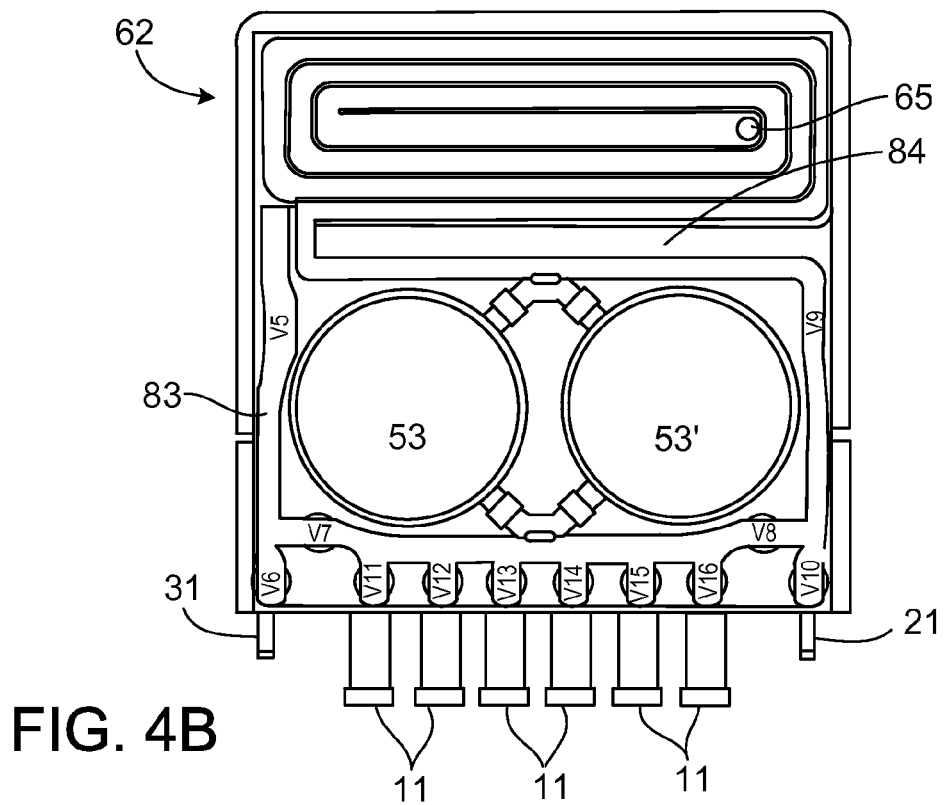

An embodiment of a cassette is shown in FIGS. 4a and 4b. It has a rigid base 101 of plastic in which the fluid paths and coupling regions are introduced as corresponding cutouts, chambers and passages. The rigid base can in this respect be produced as an injection molded part or as a deep drawn part. The coupling plane of the rigid base 101 is covered by a flexible film 102 which is welded to the rigid base in a marginal region.

During the treatment, the flexible film 102 is pressed with the rigid base by the pressing of the cassette with a coupling surface of the dialysis machine. The fluid paths within the cassette are separated from one another in a fluid tight manner by the pressing of the flexible film with the web regions of the rigid base.

The cassette has connections for the connection of the cassette to the other fluid paths. On the one hand, a connection 21 is provided for the connection to the drain bag 20 as well as a connection 31 for the connection to the connector 30. Corresponding hose elements (not shown in FIG. 4a) can be provided at these connections. The cassette also has a plurality of connections 11 for the connection of dialysate containers 10. The connections 11 are designed as connectors to which corresponding connector elements can be connected.

The connections are in each case in connection with fluid paths within the cassette. Valve regions are provided in these fluid paths. In these valve regions, the flexible film 102 can be pressed into the rigid base 101 via valve actuators at the machine side such that the corresponding fluid path is blocked. The cassette in this respect first has a corresponding valve for each connection via which this connection can be opened or closed. The valve V10 is associated with the connection 21 for the drain bag 20, and the valve V6 is associated with the connection 31 for the patient connector 30. The valves V11 to V16 are associated with the connections 11 for the dialysate container 10.

Pump chambers 53 and 53' are provided in the cassette via which corresponding pump actuators of the dialysis machine can be actuated. The pump chambers 53 and 53' are concave cut-outs in the rigid base 101 which are covered by the flexible film 102. The film can be pressed into the pump chambers 53 and 53' or pulled out of these pump chambers again by pump actuators of the dialysis machine. A pump flow through the cassette can hereby be generated in cooperation with the valves V1 to V4 which connect the accesses and outflows of the pump chambers 53 and 53' and are designated by the reference numeral 73 in FIG. 4*a*. The pump chambers can in this respect be connected via corresponding valve circuits to all connections of the cassette.

A heating region 62 is also integrated into the cassette. In this region, the cassette is brought into contact with or close proximity to heating elements of the dialysis machine which heat the dialysate flowing through this region of the cassette. The heating region 62 in this respect has a passage for the dialysate which extends spirally over the heating region 62. The passage is formed by webs 64 of the rigid base which are covered by the flexible film 102.

The heating region 62 is provided at both sides of the cassette. A flexible film is also arranged at the rigid base in the heating region at the lower side 63 of the cassette for this purpose. The flexible film is also welded to the rigid base in a marginal region. A passage is likewise arranged at the lower side and the dialysate flows through it. The passages on the lower side and on the upper side are formed by a middle plate of the rigid base which separates the upper side from the lower side and on which webs are downwardly and upwardly provided which form the passage walls. In this respect, the dialysate first flows spirally on the upper side up to the aperture 65 through the middle plate from where the dialysate flows back to the lower side through the corresponding passage. The heating surface which is available for the heating of the fluid can be correspondingly enlarged by the heating region provided at the upper side and at the lower side. Alternatively, the heating region can be arranged on only one side of the cassette.

The cassette also has sensor regions 83 and 84 by which temperature sensors of the dialysis machine can be coupled to the cassette. The temperature sensors in this respect lie on the flexible film 102 and can thus measure the temperature of the liquid flowing through the passage disposed below. Two temperature sensors 84 are arranged at the inlet of the heating region. A temperature sensor 83 via which the temperature of the dialysate pumped to the patient can be measured is provided at the outlet at the patient side.

Figure 5:
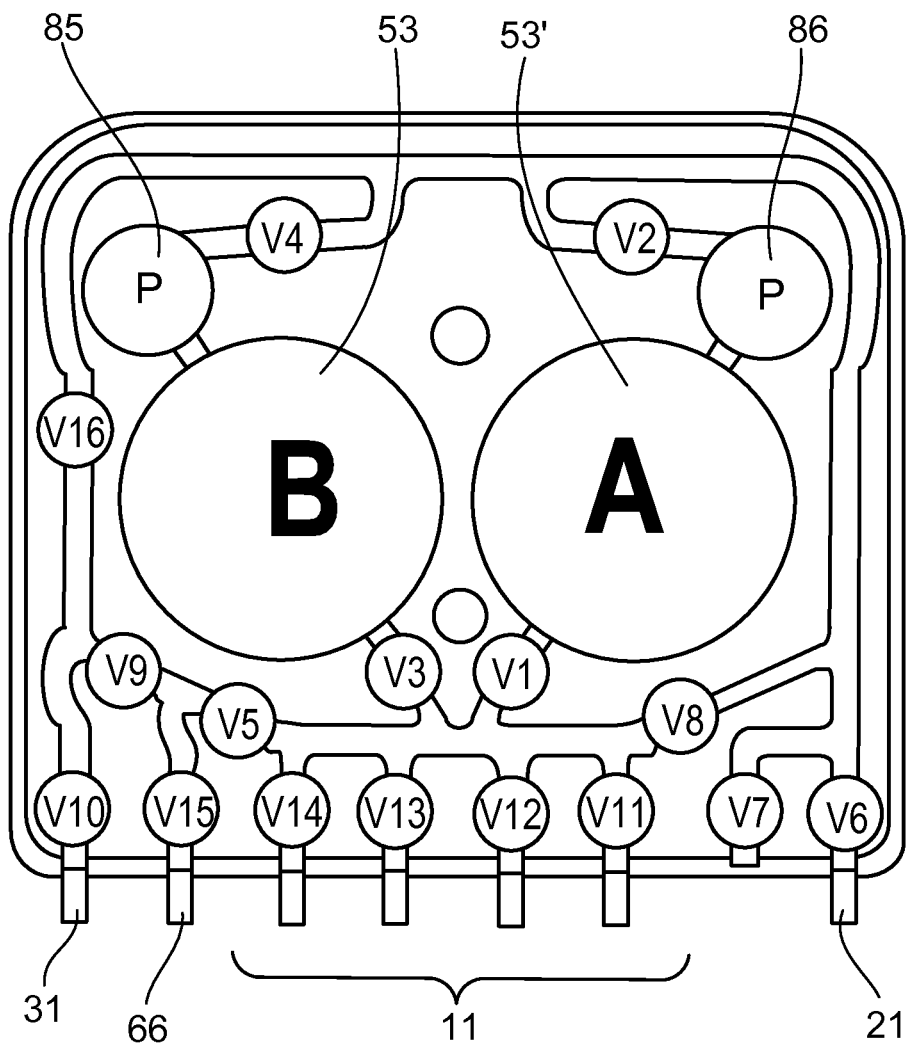
FIG. 5 is a plan view of a second embodiment of a cassette.

Another embodiment for a cassette is shown in FIG. 5. The cassette in this respect substantially corresponds in its design to the cassette of FIGS. 4*a* and 4*b*, but does not include any heating region. During use of this cassette, the heating therefore does not take place via a heating region integrated into the cassette, but rather via a heating bag which is placed onto a heating plate of the dialysis machine or in some other manner.

The cassette shown in FIG. 5 has fluid paths which can be opened and closed via valve regions which are numbered consecutively from V1 to V16. The cassette also has connections for the connection to further components of the fluid system. In this respect, the connection 21 is provided for the connection to the drain bag 20 and the connection 31 is provided for connection to the connector 30 to the patient. Connections 11 are also provided for the connection of dialysate containers 10.

Unlike the cassette of FIGS. 4*a* and 4*b*, the cassette shown in FIG. 5 has a further connection 66 for the connection of a heating bag. In this respect, the liquid can be pumped into a heating bag via the connection 66 for the heating of the fluid from the dialysate containers 10. This heating bag typically lies on a heating element so that the fluid present in the heating bag can be heated. The fluid is thereupon pumped from the heating bag to the patient.

The pump chambers 53 and 53' and the valves V1 to V4 correspond in design and function to the corresponding components of the cassette of FIGS. 4*a* and 4*b*.

The cassette of FIG. 5 does not have any sensor region for the connection of a temperature sensor. It is rather arranged in the region of the heating elements. The cassette, however, has measurement regions 85 and 86 for the measurement of the pressure in the pump chambers 53 and 53'. The measurement regions 85 and 86 are in this respect chambers which are in fluid communication with the pump chambers and are likewise covered by the flexible film. Pressure sensors at the apparatus side which measure the pressure in the measurement chambers 85 and 86 and thus in the pump chambers 53 and 53' can be coupled to the measurement regions.

The connection of the connections 11, 21, 31 and 66 of the cassette to the further components of the fluid system takes place via hose connections. Connectors are optionally arranged at these hose connections.

1.3 Hoses

The connection between the individual containers of the system, the cassette and the patient connector usually takes place via hose connections. Since they are in each case disposable articles, the hoses are usually already fixedly connected at at least one side to a further element. Hoses can, for example, already be provided at one or more of the connections of the cassette. Hoses can likewise already be in fixed communication with bags.

1.4 Connections

The fluid system is usually divided into a plurality of parts and packaged in sterile form. These parts first have to be connected to one another for the treatment. The cassette and the dialysate bag or bags are in this respect in particular packaged separately from one another.

The connections between the individual elements of the fluid system usually takes place via connectors. The connectors are in this case designed so that they enable a sterile connection between the individual components. This can occur, for example, via corresponding protective films which are automatically opened on the closing of the connector.

The connection of the individual components can take place manually by an operator or by the patient him or herself. Provision can alternatively be made that the connection of the individual components is carried out automatically by the dialysis machine.

For this purpose, the corresponding connectors can be placed into a connector receiver of the dialysis machine and can be automatically joined together by the dialysis machine.

An electronic control can furthermore be provided which monitors that the correct components of the system are connected to one another. Identification means such as barcodes or RFIDs which identify the components can be provided at the connectors for this purpose. The dialysis machine in this respect includes an identification means detection unit such as a barcode reader or an RFID detection unit which detects the identification means on the connectors. The controller of the peritoneal dialysis can hereby recognize whether the correct connectors were inserted.

Such a check of the correct assembly of the fluid system can be combined with an automatic connection of the connectors. The system thus first checks whether the correct connectors were placed into the connector receivers. The connection between the connectors is only established by the dialysis machine when the correct connectors were inserted. Otherwise, the dialysis machine draws the attention of the user to the fact that the wrong connectors have been inserted.

2. The Dialysis Machine

The individual components of a dialysis machine will now be described in more detail.

Figure 6:
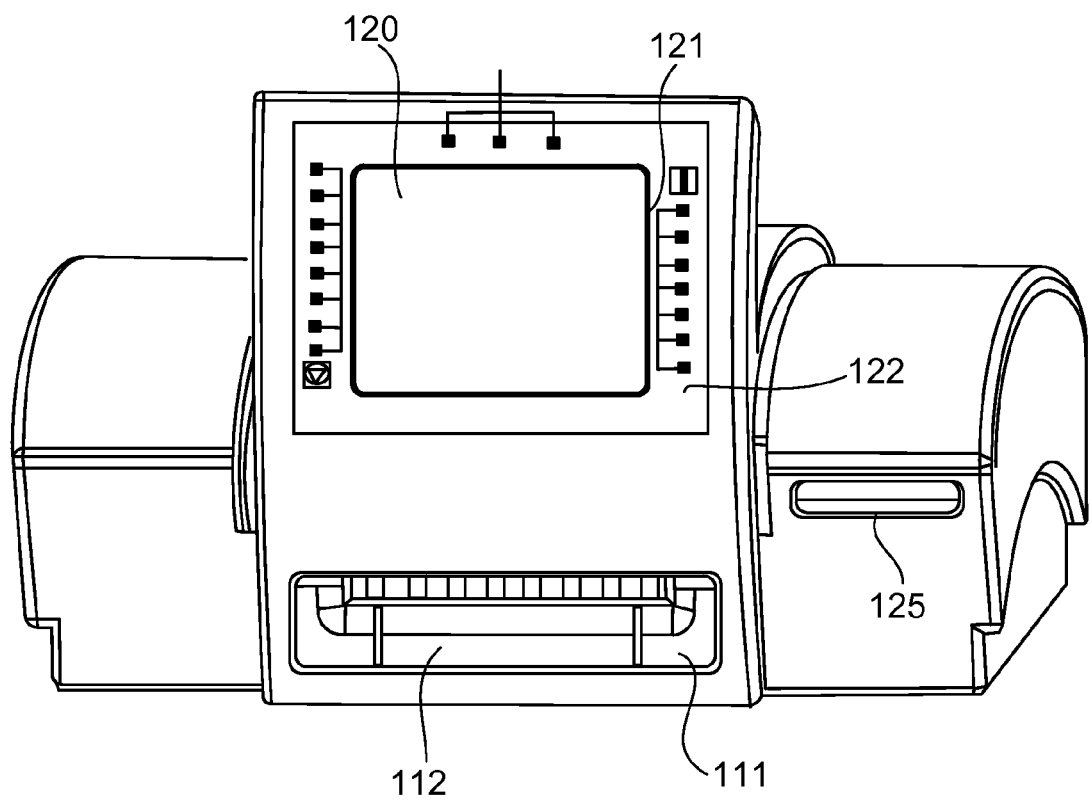
FIG. 6 is a perspective view of a first embodiment of a dialysis machine.
Figure 7:
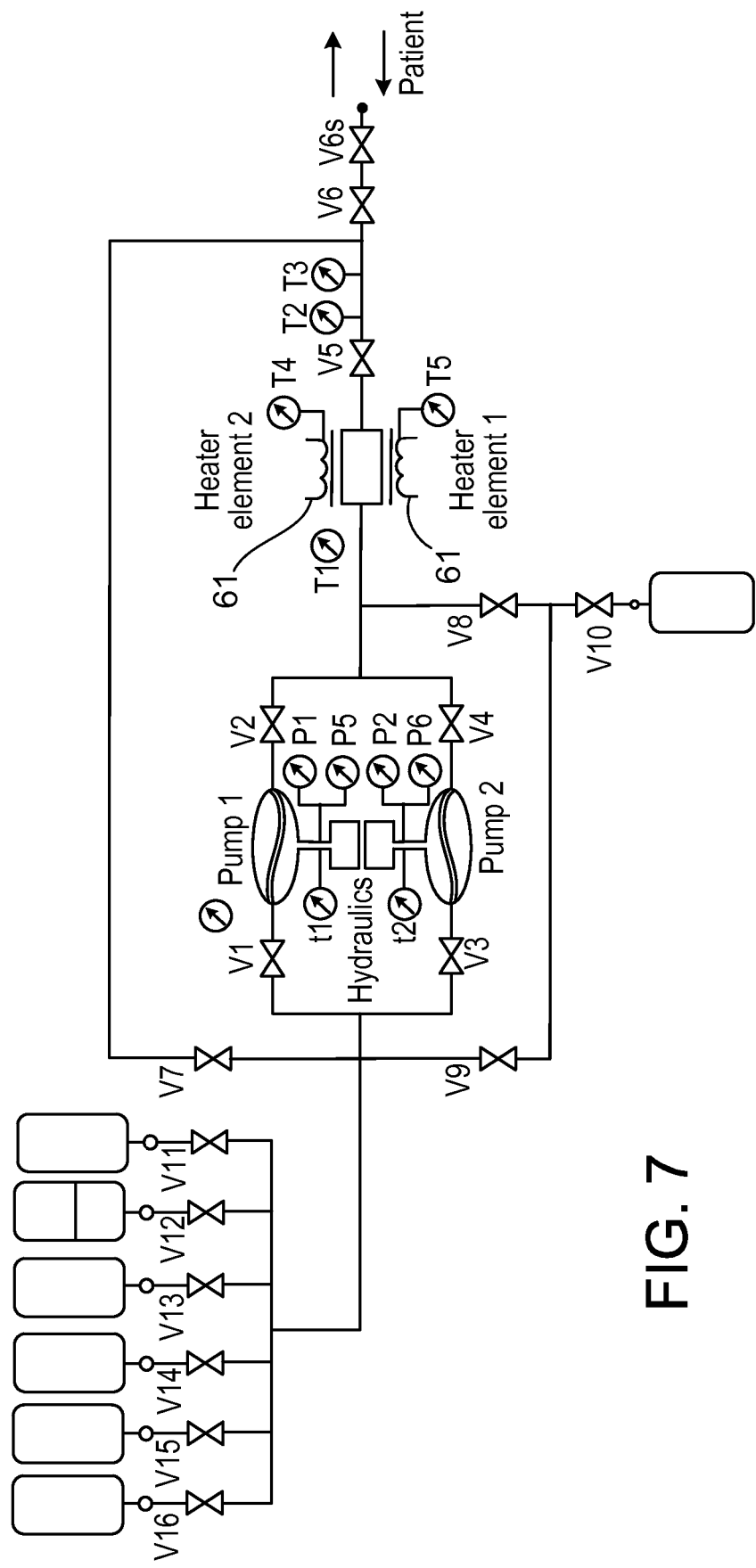
FIG. 7 is a schematic fluid flowchart of a first embodiment of a peritoneal dialysis system.

An embodiment of a dialysis machine is shown in FIG. 6 in which the cassette of FIGS. 4*a* and 4*b* is used. A schematic illustration of the peritoneal dialysis system resulting from this dialysis machine and the cassette of FIGS. 4*a* and 4*b* is shown in FIG. 7.

Figure 8:
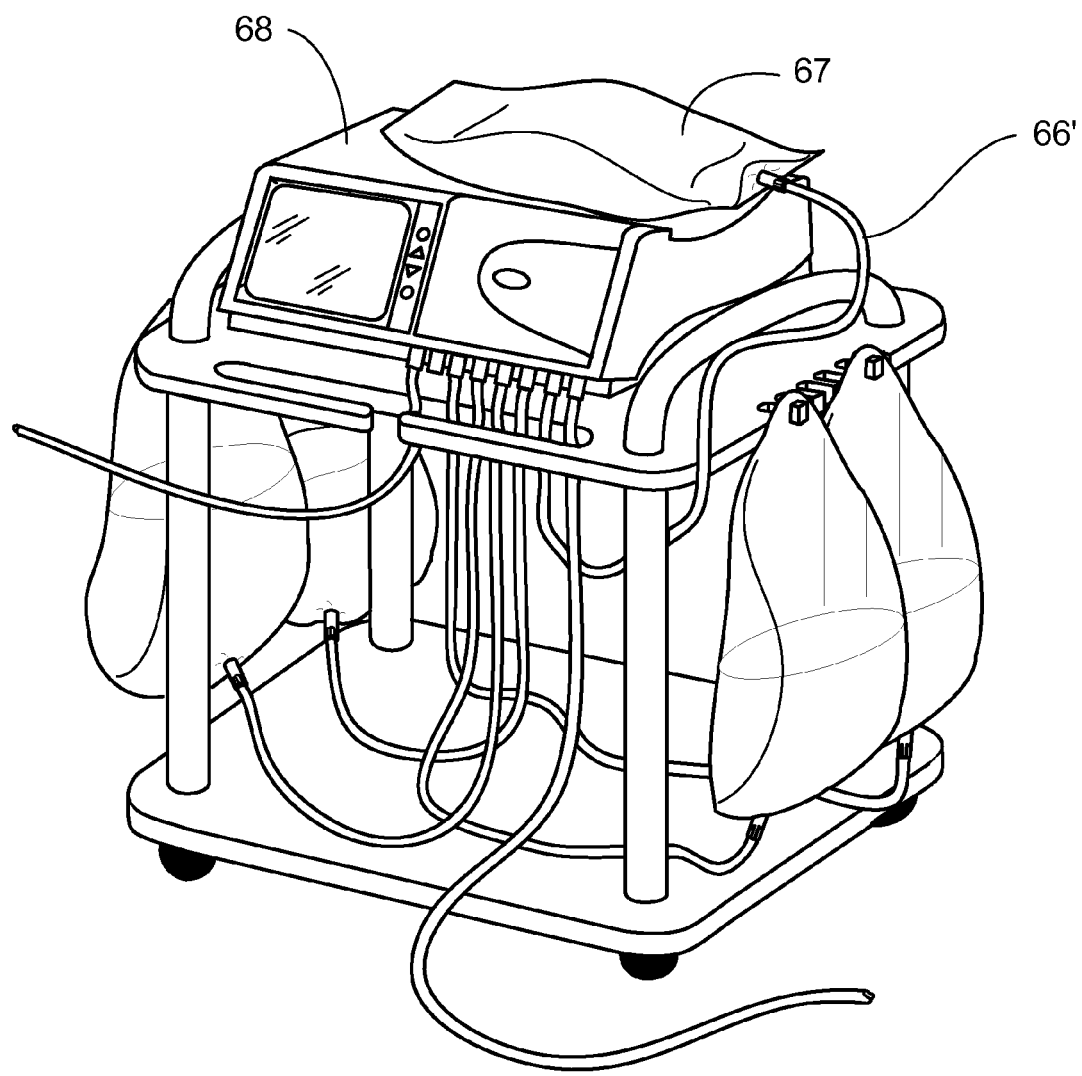
FIG. 8 is a perspective view of a second embodiment of a dialysis machine.
Figure 9:
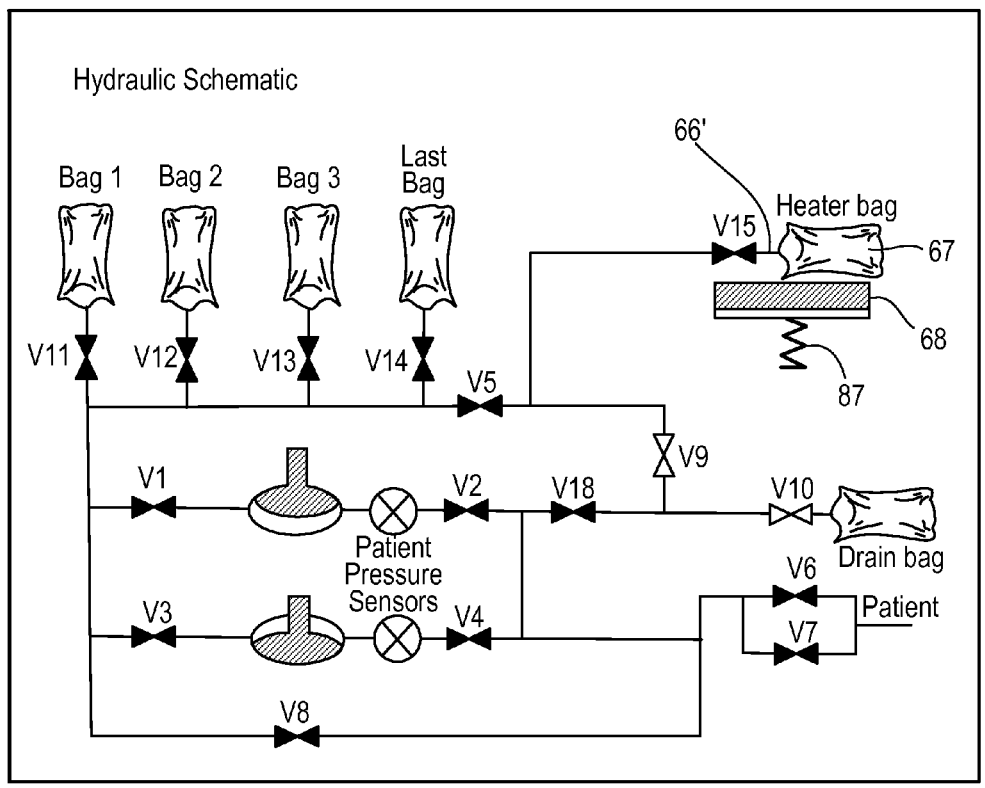
FIG. 9 is a schematic fluid flowchart of a second embodiment of a peritoneal dialysis system.

Another embodiment of a dialysis machine is shown in FIG. 8 in which the cassette of FIG. 5 is used. The dialysis system resulting from the combination of this dialysis machine and the cassette of FIG. 5 is schematically illustrated in FIG. 9.

The two above-noted dialysis systems differ in the design of the heater, in the coupling between the dialysis machine and the cassette, and in the design of the actuators and sensors.

2.1 Heater

The fresh dialysate has to be brought to body temperature before it is conveyed into the abdomen of the patient. The dialysis machine has a corresponding heater for this purpose.

The heating in this respect usually takes place via one or more heating elements. The heating elements can, for example, be ceramic heating elements. With such ceramic heating elements, a resistance strip is applied to a ceramic carrier. The heating strip is heated by the application of a voltage to it, whereby the ceramic carrier material is also heated. The ceramic heating element is in this respect usually arranged on a heating plate. It can be made of aluminum, for example. The fluid paths are in turn coupled to the heating plate so that the dialysate present in the fluid paths can be heated. Two different designs are available for the heating of the fluid. On the one hand, a larger quantity of dialysate can first be heated which is only pumped to the patient after the heating phase. This usually takes place via a heating bag which is placed on a heating plate of the dialyzer.

The heating bag can in this respect be the dialysis bag in which the dialysate is provided. Usually, however, a separate heating bag is used in which the dialysate is pumped for heating. If the dialysate is heated in the heating bag, it is pumped to the patient from there.

Such a concept is realized in the dialysis machine shown in FIGS. 8 and 9. In this respect, a heating bag 67 is provided which lies on a heating plate 68. The heating plate 68 is arranged on the upper side of the peritoneal dialysis machine so that it is easily accessible. The heating bag 67 is connected to the cassette via a line 66'. The cassette has the valves V5, V9 and V15 via which the heating bag 67 can be connected to the other components of the fluid system. Fresh dialysate can thus be pumped from the dialysate containers 10 via the pump chambers to the heating bag 67. At the start of a treatment, the heating bag 67 is first filled with unheated dialysate. The dialysate in the heating bag 67 is then heated to body temperature via the heating plate 68. The dialysate is then pumped to the patient via the pump chambers. The heating bag 67 can thereupon be filled again so that the dialysate quantity required for the next treatment cycle can be heated.

A temperature sensor 88, which is in contact with the heating bag 67 and can thus measure the temperature of the dialysate in the heating bag 67, is advantageously provided in the region of the heating plate 68. A temperature sensor can also be provided at the heating plate or at the heating element which measures the temperature of the heating element or of the heating plate. A corresponding controller makes sure that the heating plate does not become too hot for the material of the bag.

The heating bag 67 can additionally take over functions in the balancing of the fluid flows. The heating plate 68 can thus be part of scales 87 via which the weight of the heating bag 67 can be determined. The fluid quantity which is supplied to the patient after heating can hereby be determined.

Alternatively to the heating of the dialysate via a heating bag, the dialysate can be heated while it is being pumped to the patient. The heating thus works in the form of a continuous-flow water heater which heats the dialysate moved through the fluid system while it is being pumped through the fluid paths.

In this concept, a dialysate passage is provided which is coupled to a heating element of the dialysis machine. While the dialysate flows through the dialysate passage, it takes up heat from the heating element of the dialysis machine while so doing.

Such a concept is implemented in the dialysis machine which is shown in FIGS. 6 and 7. The heating region is integrated in the cassette in this respect, as was already shown above. On the coupling of the cassette to the dialysis machine, the heating region of the cassette comes thermally into contact with heating elements of the dialysis machine.

The heating elements can in this respect likewise be designed as ceramic heating elements and can be in contact with heating plates which are coupled to the heating region of the cassette. As already shown with respect to the cassette, a respective heating plate which heats the dialysate flowing through the heating region is in contact both with the upper side and with the lower side of the heating region.

Respective temperature sensor regions are provided in the cassette at the inflow and at the outflow of the heating region and come into contact with temperature sensors of the peritoneal dialysate by the coupling of the cassette. The temperature of the dialysate flowing into the heating region and the temperature of the dialysate flowing out of the heating region can thus be determined by the temperature sensors T1 to T3. Temperature sensors T4 and T5 are also provided to determine the temperature of the heating elements and/or of the heating plates.

To enable a coupling of the actuators and/or sensors of the dialysis machine to the corresponding regions of the cassette, the dialysis machine has a cassette receiver with a coupling surface to which the cassette can be coupled. The corresponding actuators, sensors and/or heating elements of the dialysis machine are arranged at the coupling surface. The cassette is pressed with this coupling surface such that the corresponding actuators, sensors and/or heating elements come into contact with the corresponding regions in the cassette.

In this respect, a mat of a flexible material, such as a silicone mat, is advantageously provided at the coupling surface of the dialysis machine. It ensures that the flexible film of the cassette is pressed with the web regions of the cassette and thus separates the fluid paths within the cassette.

A peripheral margin of the coupling surface is advantageously provided which is pressed with the marginal region of the cassette. The pressing in this respect advantageously takes place in an airtight manner so that an underpressure or vacuum can be built up between the coupling surface and the cassette.

A vacuum system can optionally be provided to pump air out of the space between the coupling surface and the cassette. A particularly good coupling of the actuators, sensors and/or heating elements of the peritoneal dialysis device with the corresponding regions of the cassette is hereby made possible. In addition, the vacuum system allows a leak tightness check of the cassette. A corresponding vacuum is applied after the coupling for this purpose and a check is made whether this vacuum is maintained.

The compression of the cassette against the coupling surface of the dialysis machine can take place pneumatically, for example. For this purpose, usually an air cushion is provided which is filled with compressed air and thus presses the cassette onto the coupling surface.

The cassette receiver usually has a receiver surface which is disposed opposite the coupling surface and into which the rigid base of the cassette is inserted. The receiver surface advantageously has corresponding recesses for this purpose. The receiver surface with the inserted cassette can then be pressed onto the coupling surface via a pneumatic pressing apparatus.

The insertion of the cassette can take place in different ways. In the dialysis machine which is shown in FIG. 6, a drawer 11 can be moved out of the dialysis machine to receive the cassette. The cassette is inserted into this drawer. The cassette is then pushed into the dialysis machine together with the drawer. The pressing of the cassette with the coupling surface which is arranged in the interior of the apparatus is carried out by moving the cassette and the coupling surface mechanically toward one another and then pressing them together pneumatically.

The coupling of a cassette 110 with the dialysis machine of FIG. 8 will now be described with reference to FIG. 10. The coupling surface 130 is freely accessible by opening a door 140 so that the cassette can be arranged at the correct position at the coupling surface 130. The coupling surface 130 is in this respect inclined rearwardly toward the vertical, which enables an easier coupling. The door 140 can then be closed so that a receiver surface at the door comes into contact with the rear side of the cassette. The pressing takes place by an air cushion arranged in the door. In addition, a vacuum is applied between the coupling surface and the cassette 110.

The dialysis machine of FIG. 6 also has an apparatus for automatic connecting. A connector receiver 112 is provided for this purpose into which the connectors of the dialysate bag 10 are inserted. The connector receiver 112 then moves into the apparatus where a barcode reader is provided which reads the barcodes applied to the connectors. The apparatus can thus check whether the correct bags were inserted. If the correct bags are recognized, the connector receiver 112 moves in completely and so connects the connectors of the bag to the connections 11 of the cassette made as connectors.

Figure 10:
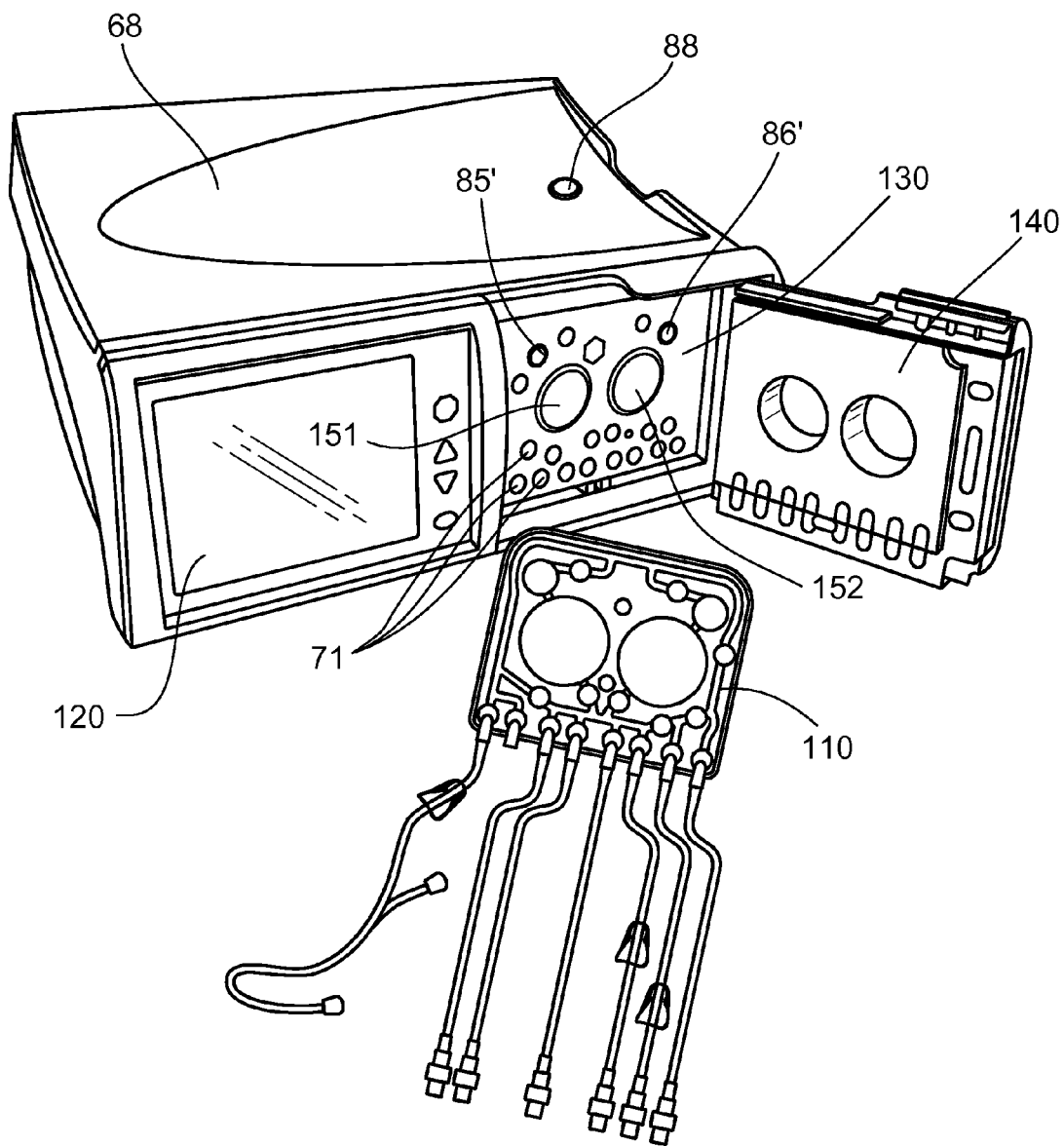
FIG. 10 illustrates the coupling of the cassette in the second embodiment of a peritoneal dialysis system.

In the dialysis system of FIG. 10, hose sections are arranged at the connections 11 of the cassette and for manual connection to the corresponding bags via connectors.

2.3 Pump Actuators

The pumping of the liquid through the fluid system takes place by a membrane pump which is formed by the pump chambers 53 and 53' together with the flexible film of the cassette. If the flexible film is pressed into the pump chamber by a corresponding pump actuator, fluid is pumped out of the pump chamber into the opened regions of the fluid paths of the cassette. Conversely, fluid is sucked out of the fluid paths and into the pump chamber by pulling the film out of the pump chamber.

The pump stroke in this respect takes place by movement of a pump actuator into the pump chamber. The pump actuator is moved away from the pump chamber again for the suction stroke. An underpressure arises in this respect due to the airtight pressing of cassette and coupling surface by which the flexible film of the cassette follows the pump actuator and is thus pulled out of the pump chamber again.

To enable a good coupling of the pump actuator to the flexible film of the cassette, a vacuum system can be provided. In this respect, the force with which the flexible film is moved away from the pump chamber at a maximum during a suction stroke can be set via the setting of a corresponding vacuum between the coupling surface and the cassette. The suction force of the pump can hereby be set very finely. The pump force is in contrast set by the thrust force of the actuator.

The balancing of the fluid flows can in this respect take place by the counting of the suction and pump strokes since the membrane pump has a high precision of the fluid quantity pumped with each stroke.

2.3.1. Hydraulic Drive

Figure 11:
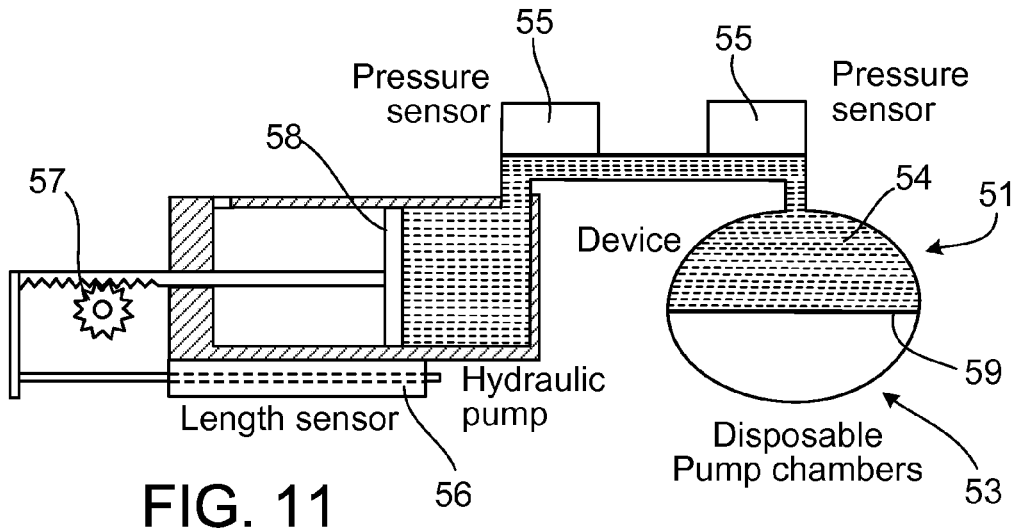
FIG. 11 illustrates a first embodiment of a pump actuator.

The structure of a first embodiment of a pump actuator is shown in FIG. 11. The pump actuator is moved hydraulically in this respect. A membrane 59 is provided for this purpose which is placed at the flexible film of the cassette. The membrane 59 can be produced, for example, from silicone. A chamber 54 which can be filled with hydraulic fluid is provided behind the membrane 59. By application of an overpressure in the chamber 54, the membrane 59, and with it the flexible film of the cassette, is pressed into the pump chamber 53 of the cassette. By application of an underpressure to the chamber 54, the membrane 59 is, in contrast, pulled into the chamber 54. Due to the underpressure between the flexible film of the chamber and the membrane, the flexible film follows this movement so that the volume of the pump chamber 53 increases. The pump process with the pump stroke and the suction stroke is shown schematically in FIG. 12*b*.

A hydraulic pump 58 is provided for the operation of the pump hydraulic. It has a cylinder in which a piston can be moved to and fro via a motor 57. The hydraulic fluid is hereby pressed into the chamber 54 or sucked out of it again via a corresponding connection line. A position encoder 56 is provided at the hydraulic pump 58 in this respect and the movement of the piston can be recorded via it. It can hereby be determined how much hydraulic fluid was pressed into the chamber 54 and how much hydraulic fluid was removed from it. Pressure sensors 55 are also provided at the hydraulic system which measure the pressure in the hydraulic system. They on the one hand allow a functional check of the hydraulic system since the data of the pressure sensors can be compared with those of the position encoder 56 and the leak tightness of the hydraulic system can hereby be checked.

In addition, the pressure sensors allow a determination of the pressure in the pump chamber 53 of the cassette. If the hydraulic pump 58 is not moved, a pressure balance is adopted between the chamber 54 and the pump chamber 53. The pressure of the hydraulic fluid thus corresponds to the pressure in the pump chamber 53.

Figure 12A:
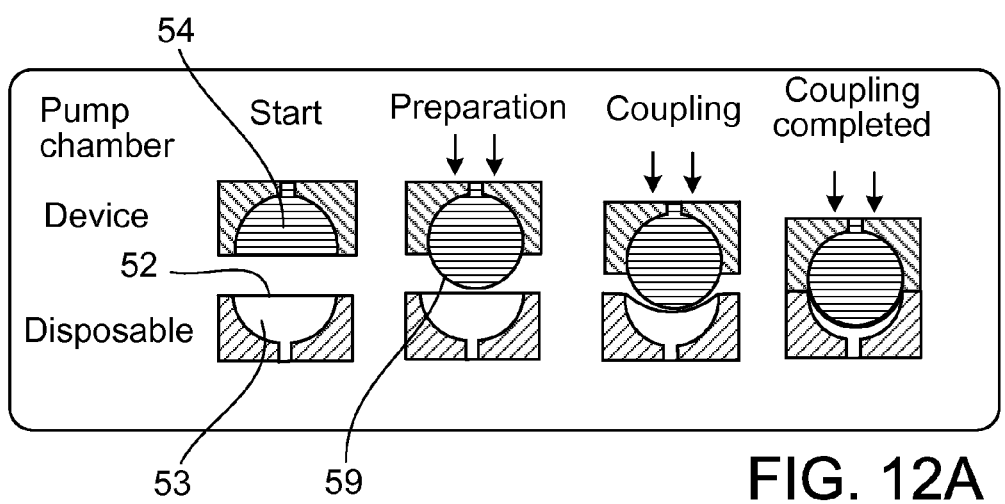
FIGS. 12a and 12b illustrate the coupling of a pumping region of the cassette to a pump actuator.
Figure 12B:
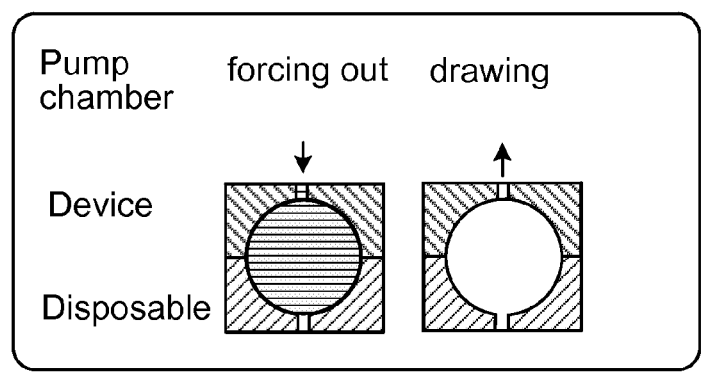

The coupling procedure of the pump actuator to the pump chamber 53 is shown in FIG. 12*a*. In this respect, the chamber 54 is first loaded with hydraulic fluid such that the membrane 59 arches outwardly for the preparation of the coupling. The coupling surface and the cassette are thereupon moved toward one another so that the membrane 59 presses the flexible film of the cassette into the pump chamber 53. After the pressing of the coupling surface and of the cassette, the space between the membrane and the flexible film is outwardly closed in an airtight manner so that the flexible film follows the movement of the membrane. This is shown in FIG. 12*b*.

The pump actuator shown in FIG. 11 is in this respect implemented in the dialysis machine of FIGS. 6 and 7. In this respect, a corresponding pump actuator is respectively provided for each of the two pump chambers 53 and 53'.

2.3.2 Electromechanical Drive

Alternatively, the pump actuator can be operated in an electric motor manner. A correspondingly shaped ram is provided for this purpose which is pressed toward or away from the flexible film via an electric motor(e.g., via a stepped motor), and the pump stroke or suction stroke is thus generated. Such pump actuators 151 and 152 are shown in the dialysis system of FIG. 10. A vacuum system is also provided which ensures that the flexible film also follows the ram in the suction movement.

2.4 Valve Actuators

A valve plunger can be provided as the valve actuator which presses the flexible film of the cassette into a corresponding chamber of the rigid base and closes the fluid passage in this region. The valve actuator can, for example, be pneumatically actuated. The plunger can in this respect be biased via a spring so that it either opens without pressure or closes without pressure.

Alternatively, the valve actuator can be implemented via a flexible membrane which is moved hydraulically or pneumatically. The flexible membrane is in this respect moved toward the cassette by application of pressure and so presses a corresponding valve region of the flexible film into a fluid passage to close it.

Valve actuators 71, which are coupled to the valve regions V1 to V16 of the cassette, can be recognized on the coupling surface in FIG. 10.

2.5 Sensors

The dialysis machine has sensors via which the machine can be controlled or its proper functioning can be monitored.

One or more temperature sensors are provided via which the temperature of the dialysate and/or of the heating elements can be measured. In the dialysis machine of FIGS. 6 and 7, the temperature sensors are arranged at the coupling surface to the cassette and can thus measure the temperature of the dialysate flowing through the cassette. In the dialysis machine of FIGS. 8-10, in contrast, a temperature sensor 88 is provided on the heating plate 68 which measures the temperature of the dialysate present in the bag 67. Temperature sensors can furthermore be provided at the heating element or elements.

One or more pressure sensors can also be provided to determine the pressure in the pump chambers. Such sensors can help to ensure that dialysate is not pumped to the patient at too high a pressure and/or that the suction pressure does not become too high upon pulling dialysate from the patient. In the dialysis machine of FIGS. 6 and 7, the pressure measurement takes place via pressure sensors in the hydraulic system of the pump actuators, as was shown above. In the dialysis machine of FIGS. 8-10, in contrast, pressure sensors 85' and 86' are provided in the coupling surface which directly measure the pressure in corresponding pressure measurement regions of the cassette. The coupling of these pressure sensors to the cassette is in this respect advantageously ensured by a vacuum system.

2.6 Input/Output Unit

The dialysis machine also includes an input/output unit for communication with an operator. A corresponding display is in this respect provided for the output of information which can, for example, be implemented by light-emitting diodes, LCD displays or a screen. Corresponding input elements are provided for the inputting of commands. Push buttons and switches can, for example, be provided in this respect.

In each of the above described dialysis machines of FIGS. 6-10, a touch screen 120 is provided which allows an interactive menu navigation. Display elements 121 and 122 are also provided which show states of the dialysis machine in compact form.

The dialysis machine of FIGS. 6 and 7 also has a card reader 125 via which a patient card can be read. Data on the treatment of the respective patient can be stored on the patient card. The treatment procedure for the respective patient can hereby be individually fixed.

The peritoneal dialysis machine also has an acoustic signal unit via which acoustic signals can be output. In this respect, an acoustic warning signal can in particular be output when an error state is registered. A loudspeaker is in this respect advantageously provided via which the acoustic signals can be generated.

2.7 Controller

The peritoneal dialysis also has a controller by which all components can be controlled and monitored. The controller provides the automatic procedure of the treatment.

Figure 13:
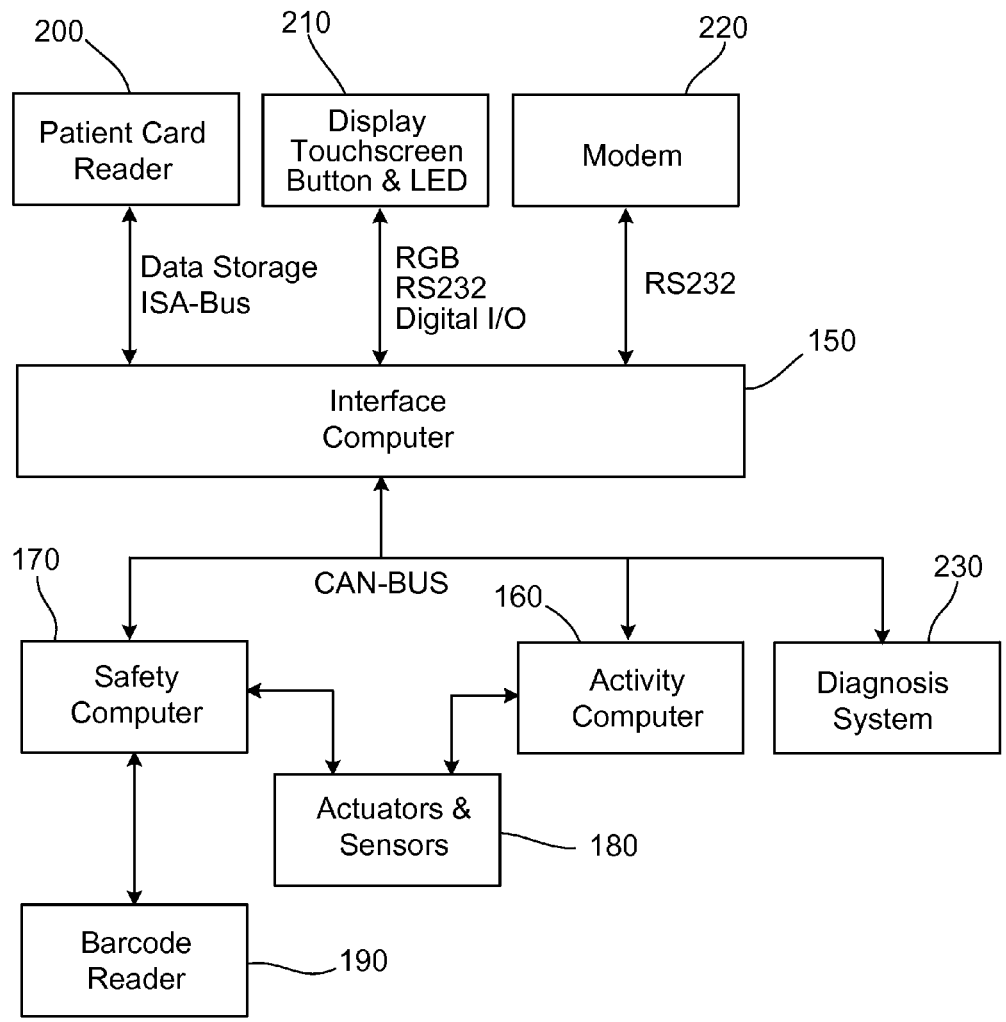
FIG. 13 is a schematic diagram of the design of an embodiment of a controller.

The basic structure of an embodiment of such a controller is shown in FIG. 13.

The communication with the operator and with external information sources in this respect takes place via an interface computer 150. It communicates with a patient card reader 200, an input and output unit (e.g., touchscreen) 210 which serves communication with the patient and with a modem 220. Updated software can, for example, be uploaded via the modem 220.

The interface computer 150 is connected via an internal bus to an activity computer 160 and to a safety computer 170. The activity computer 160 and the safety computer 170 generate redundancy of the system. The activity computer 160 in this respect receives signals from the sensors of the system and calculates the control signals for the actuators 180. The safety computer 170 likewise receives signals from the sensors 180 and checks whether the commands output by the activity computer 160 are correct. If the safety computer 170 determines an error, it initiates a corresponding emergency procedure. The safety computer 170 can in particular trigger an alarm signal in this respect. The safety computer 170 can furthermore close the access to the patient. A special valve is arranged at the output of the cassette at the patient side for this purpose and only the safety computer 170 has access to it. This safety valve is in this respect closed in the pressureless state so that it closes automatically on a failure of the pneumatic system.

The safety computer 170 is also connected to the barcode reader 190 and so checks the connection of the correct dialysis bags.

A diagnosis system 230 is furthermore provided via which errors of the system can be determined and remedied.

3. Heating Systems and Methods

Heating systems and methods that can be used in one of the dialysis systems presented above or in one of the dialysis machines presented above will now be described. The heating systems and methods described can, for example, be used for the control of a heater as was described in Section 2.1.

Figure 14:
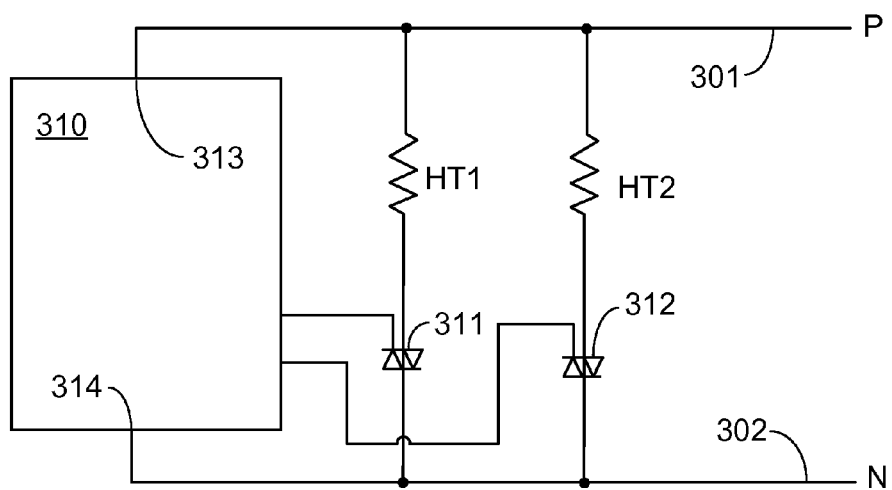
FIG. 14 illustrates a first embodiment of a heater that includes two heating elements.

FIG. 14 shows an embodiment of a heating control unit 310 by which two heating elements HT1 and HT2 of a heater are controlled. The heating control unit includes a first switching element 311 by which the first heating element HT1 can be switched on and off and a second switching element 312 by which the second heating element HT2 can be switched on and off. In this respect, mains voltage applied at the supply lines 301 and 302 is applied at or removed from the two heating elements by the switching elements 311 and 312. The two switching elements 311 and 312 are in this respect controlled by the heating control unit 310 and thus form a switching arrangement. The switching elements 311 and 312 can, for example, be triacs. The mains voltage can in this respect be applied to the two lines 301 and 302 without a galvanic isolation. Alternatively, the mains voltage can be applied to the lines 301 and 302 via a galvanic isolation, for example via an isolating transformer.

The heating control unit 310 also has measuring connections 313 and 314 for connection to the mains voltage. In this respect, a monitoring arrangement is provided which recognizes the zero crossings of the mains voltage. The switching arrangement can in each case be actuated in the zero crossing of the mains voltage to switch the heating elements on or off. In this respect, the power of the heating is controlled via the switching on and off of one or more half cycles of the mains voltage, for example via the ratio of the half cycles with switched on heating elements to the number of the half cycles with switched off heating elements.

The two heating elements HT1 and HT2 can be switched on and off independently of one another by the switching arrangement. In alternative embodiments, only one heating element HT1 or HT2 is provided.

A control can thus be realized by the corresponding setting of the number of the half cycles with a switched on heating element or switched on heating elements which makes it possible to realize between 0 and 100% of the heating power. A temperature regulation can be provided in this respect in which the ratio of the number of the half cycles with a switched on heating element to the number of the half cycles with a switched off heating element is set on the basis of a temperature sensor reading.

The heater can be operated at different rated voltages of the mains power supply. The monitoring arrangement of the heating control unit 310 measures the level of the mains voltage and accordingly adapts the control of the heating element or elements to the found level of the mains supply. A desired power can hereby also be set precisely with different and/or fluctuating mains voltages and the same maximum power of the heating can be achieved at different mains voltages. Such an adaptation to different mains voltages is advantageously combined with a temperature regulation in this respect.

The use of two heating elements HT1 and HT2 controllable independently of one another in this respect enables a particularly favorable adaptation to different mains voltages. The two heating elements can in this respect be operated simultaneously in a first operating mode. Both heating elements can, for example, have mains voltage half cycles applied synchronously in this respect. In this operating mode, the two heating elements therefore work essentially as two heating elements connected in parallel and having only one control. Such an operating mode can be used with a low mains voltage of, for example, 100 V or 120 V in order also to provide sufficient maximum heating power at such a low mains voltage. The control in this respect advantageously switches into the first operating mode when it recognizes a mains AC voltage in a first voltage range which advantageously includes voltages of 100 V and 120 V. In some embodiments, the first voltage range extends from 80 V to 160 V. In order to set the heating power to a desired value, the two heating elements can be switched off both synchronously and alternately to set the corresponding ratio of the number of the half cycles with a switched on heating element to the number of the half cycles with a switched off heating element to the desired value.

If it is a case of two heating elements of identical rated power, the number of the half cycles with a switched on first heating element HT1 and the number of the half cycles with a switched on second heating element HT2 can be added for calculating this ratio. The number of the half cycles with switched off heating elements can equally be added. If the two heating elements in contrast have different rated powers, this has to be taken into account by a corresponding factor.

In the second operating mode, the two heating elements HT1 and HT2 in contrast each alternately have mains voltage half cycles applied. This second operating mode is used with a rated voltage of 230 V or 240 V. The control in this respect advantageously switches into the second operating mode when it recognizes a mains AC voltage in a second voltage range which includes higher voltages than the first voltage range. The second voltage range can include voltages of 230 V and 240 V. In some embodiments, the first voltage range extends from a voltage larger than 160 V onward. Since mains voltage is applied in each case at a maximum to one of the two heating elements in the second operating mode, the maximum current power consumption can be kept below the permitted amperage of, for example, 16 A. To set the maximum heating power in this respect to a desired value, for example to the maximum heating power in the first operating mode, the two heating elements can also both be switched off to set the corresponding ratio of the number of the half cycles with a switched on heating element to the number of the half cycles with a switched off heating element to a desired value.

Figures 15A, 15B:
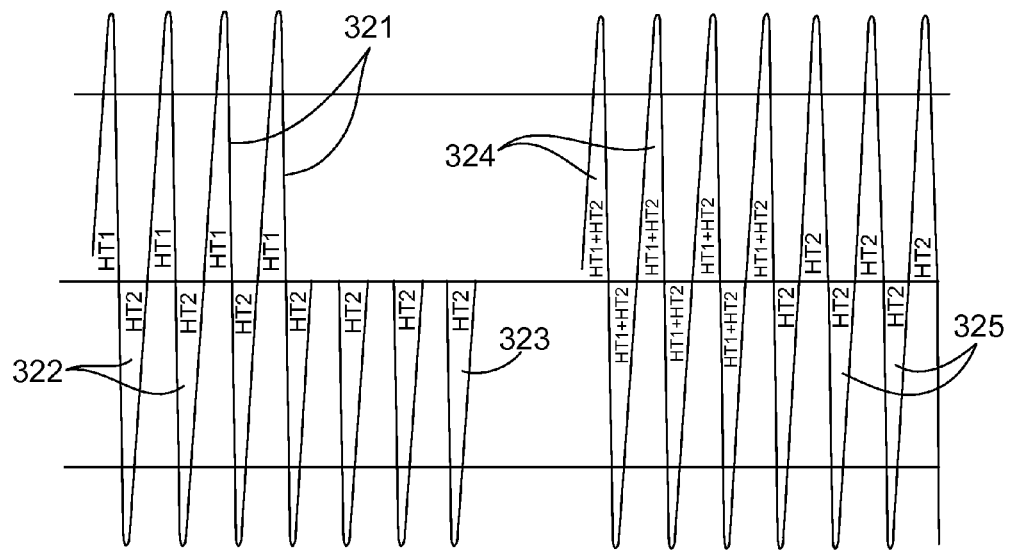
FIGS. 15a and 15b are diagrams which show the mains voltage half cycles applied to the two heating elements of the heater shown in FIG. 14 in two different operating modes.

Embodiments for a second operation mode and for a first operating mode are shown in FIGS. 15a and 15b. In the second operating mode, respective individual half cycles are switched alternately to the first heating element HT1 and to the second heating element HT2 in FIG. 15a. As shown in FIG. 15a, in this respect the upper half cycles 321 are switched to the first heating element HT1, and the lower half cycles 322 are switched to the second heating element HT2. The switch over could, however, take place in each case after a larger number of half cycles. In a subsequent time section, only the lower half cycles 323 are switched to the second heating element HT2, whereas the upper half cycles remain completely switched off. In this respect, individual half cycles could also be switched off so that there are breaks in each case between the alternating action on the first heating element and on the second heating element in which half cycles remain completely switched off.

In the first operating mode illustrated in FIG. 15b, in contrast, both the upper half cycles 324 and the lower half cycles 325 are switched to both heating elements HT1 and HT2. A correspondingly higher power can hereby be provided.

In some embodiments, the control makes the determination whether a control of the heating elements HT1 and HT2 takes place synchronously (e.g. in each case in parallel with full cycles) or alternately (e.g. in each case with half cycles) in dependence on the detected mains AC voltage. The heating is in this respect configured so that the full heating power can be provided in synchronous operation at a minimum operating voltage (e.g., 80 V) and a duty cycle of 100%. From a predetermined limit voltage (e.g., 160 V) onward, the heating elements are in contrast each operated alternately, with the heating elements alternately controlled separately with a half cycle (positively or negatively).

An adaptation of the power to the operating voltage above the minimum operating voltage takes place by a corresponding reduction of the transmitted full cycles or half cycles, with the heating power being reduced by 50% with respect to synchronous operation in the second operating mode.

The heating elements can in particular be ohmic heating elements. They can, for example, have a resistance between 10 and 50 ohms. The desired maximum heating power in this respect in particular amounts to between 200 W and 2000 W, for example, in particular to approximately 800 W.

Two alternative embodiments will now be specifically described. The maximum desired heating power should in this respect amount to 800 W in each case.

In a first embodiment, two heating elements having a resistance of 16 ohms are used. They can provide the desired heating power of 800 W with a rated voltage of 110 V, also when taking account of an undervoltage of 80 V in the first operating mode, with a current of 10 A resulting. In this respect, both heating elements are controlled in parallel with the full sine wave. If the voltage is actually 110 V, a heating power of 1512 W would result with a full control of both heating elements. In accordance with the measured voltage, individual half cycles are accordingly therefore switched off either at one heating element or at both of the heating elements to set the maximum heating power to the desired 800 W. At a voltage of 100 V, around 52% of all voltage half cycles are therefore actually switched on and the others are switched off.

At a voltage of 240 V, work is carried out in the second operating mode in which always, at a maximum, one of the two heating elements is switched on. At a resistance of the heating elements of 16 ohms in each case, a maximum current flow of 15 A results in this respect.

In an operation in which each half cycle is switched either to the one heating element or to the heating element a heating power would in this process result of 3600 W. In dependence on the mains voltage, a corresponding number of half cycles is therefore completely suppressed to set the heating power to the desired maximum value of 800 W. At an actual rated voltage of 240 V, only 22% of all the half cycles are therefore switched either to the one or to the other heating element so that the averaged amperage falls accordingly. Only 11% of the heating power or of the half cycles available in the equiphase full cycle operation is thus used.

In the second specific embodiment, two heating elements, each having 25 ohms, are used. At an effective mains voltage of 100 V, such as is present in Japan, each of the two heating elements thus has a maximum heating power of 400 W. In the first operating mode, in which both heating elements are controlled in an equiphase manner in full cycle operation, exactly the desired heating power of 800 W thus results.

At an effective mains voltage of 120 V, such as is found in the United States, a maximum power of 576 W in contrast results for each of the two heating elements in equiphase fully cycle operation. To reduce the total power down to 800 W, the number of the half cycles of the mains voltage used for heating the heating elements is therefore reduced accordingly by a complete switching off of individual half cycles. In this respect, work can continue in equiphase and individual ones of the half cycles can be completely switched off or individual half cycles can only be switched off for one of the two heating elements. The reduction in the power to the desired 400 W in this respect results from the use of only 69% of all half cycles.

Only 177 pulses are therefore used for heating in relation to 255 pulses. At a rated voltage of 240 V, the heating is, in contrast, operated in the second operating mode in which the first and the second heating elements are each operated alternately. If each half cycle were used here for operating one of the two heating elements, this would result in a heating power of approximately 2300 W. To reduce the heating power to the desired 800 W, a corresponding portion of half cycles therefore has to be completely suppressed so that only around 35% of all half cycles are used at one of the two heating elements and thus only around 17% of the heating power or half cycles available in equiphase full cycle operation is used.

The half cycles or packets of half cycles are in this respect advantageously switched so that no temperature fluctuation occurs at the heating element, that is, the switching should take place faster than the sluggishness of the heating elements.

For example, the control can take place in this respect so that the ratio of the half cycles with a switched on heating element and with a switched off heating element is in each case kept to a desired value averaged over a specific number of pulses or a specific time. The ratio can, for example, in this respect be set over a period of, for example, 255 half cycles.

In this respect, the present invention is, however, not restricted to switching individual half cycles. Pulse packets having a plurality of half cycles can rather likewise be switched.

A number of embodiments of the invention have been described. Nevertheless, it will be understood that various modifications may be made without departing from the spirit and scope of the invention. Other embodiments are within the scope of the following claims.

What is claimed is:
1. A dialysis machine comprising:
a pump for pumping a medical liquid;
a heater for heating the medical liquid, the heater having at least one heating element and
a heating control unit, which is configured to be connected to mains AC voltage, connected to the heater,
the heating control unit comprising
a monitoring arrangement configured to recognize zero crossings of the mains AC voltage and to detect a level of the mains AC voltage and
a switching arrangement configured to switch the at least one heating element on or off in the zero crossing,
wherein the heating control unit is configured to control power of the heater by switching on and off one or more half cycles of the mains AC voltage,
a temperature sensor,
wherein the heating control unit is configured to set a ratio of a number of half cycles with a switched on heating element to a number of half cycles with a switched off heating element based on a signal of the temperature sensor and the detected level of the mains AC voltage.

2. The dialysis machine of claim 1, wherein the heater comprises two heating elements, wherein the two heating elements are operated partly or fully synchronously.

3. The dialysis machine of claim 1, wherein the heating control unit generates and superimposes a control signal based on a signal of the temperature sensor on a control signal for adapting the power to the detected level of the mains AC voltage.

4. The dialysis machine of claim 1, wherein the ratio of the number of half cycles with a switched on heating element to the number of half cycles with a switched off heating element is set smoothly in time and directly in dependence on the signal of the temperature sensor and of the detected level of the mains power supply.

5. The dialysis machine of claim 1, wherein the temperature sensor determines the temperature of the medical liquid to be heated.

6. The dialysis machine of claim 1, wherein the dialysis machine is a peritoneal dialysis machine and the heater is configured to heat dialysate.

7. The dialysis machine of claim 6, wherein the temperature sensor determines the temperature of the dialysate.

8. The dialysis machine of claim 1, further comprising a cassette for controlling the flow of the medical liquid, the cassette being coupled to a coupling surface of the dialysis machine and comprising at least one pumping chamber of the pump.

9. The dialysis machine of claim 8, wherein the cassette comprises a heating region that is in contact with the heating element of the dialysis machine.

10. The dialysis machine of claim 9, wherein the temperature sensor is provided in the coupling surface of the dialysis machine and contacts a temperature sensor region of the cassette located at the inflow or at the outflow of the heating region in order to measure the temperature of the medical liquid flowing in or out of the heating region of the cassette.

11. The dialysis machine of claim 8, further comprising a heating bag connected to the cassette, the heating element being arranged in a heating plate that contacts the heating bag.

12. The dialysis machine of claim 11, wherein the temperature sensor is arranged in the heating plate to contact the heating bag in order to measure the temperature of the medical liquid in the bag.

13. A method of operating a dialysis machine comprising a pump for pumping a medical liquid and a heater for heating the medical liquid, the method comprising:
   detecting zero crossings and a level of a mains AC voltage; and
   switching at least one heating element of the heater on or off in the zero crossing, wherein a power of the heater is controlled based on a number of the half cycles of the mains AC voltage with a switched on heating element, wherein a level of the mains AC voltage is detected, and wherein a ratio of the number of the half cycles with a switched on heating element to a number of a half cycles with a switched off heating element is set based on a signal of the detected level of the mains AC voltage.

14. A dialysis machine comprising:
   a pump for pumping a medical liquid;
   a heater for heating the medical liquid, the heater having at least one heating element and
   a heating control unit, which is configured to be connected to mains AC voltage, connected to the heater,
   the heating control unit comprising
   a monitoring arrangement configured to recognize zero crossings of the mains AC voltage and to detect a level of the mains AC voltage and
   a switching arrangement configured to switch the at least one heating element on or off in the zero crossing, wherein the heating control unit is configured to control power of the heater by switching on and off one or more half cycles of the mains AC voltage,
   wherein the heating control unit is configured to set a ratio of a number of half cycles with a switched on heating element to a number of half cycles with a switched off heating element based on the detected level of the mains AC voltage.

15. The dialysis machine of claim 14, wherein the monitoring arrangement and the heating control unit are configured to adapt power of the heater to fluctuating voltage levels of the mains power supply, so that the same maximum power of the heating is available independently of the level of the mains power supply.

16. The dialysis machine of claim 14, wherein the heater comprises two heating elements that can be operated in a first and a second operating mode, wherein the heating control selects the first operating mode on detection of a mains AC voltage which is in a first, lower voltage range and the second operating mode on detection of a mains AC voltage in a second, higher voltage range.

17. The dialysis machine of claim 16, wherein, while operating in the first or second operating mode, the heater control sets the ratio of the number of the half cycles with a switched on heating element to the number of the half cycles with a switched off heating element in dependence on the level of the detected mains AC voltage within the respective voltage range in which an operation takes place in the first or second operating mode, thereby keeping the maximum power of the heating constant or setting a desired power irrespective of voltage fluctuations within the respective voltage range.

18. The dialysis machine of claim 14, wherein the ratio of the number of half cycles with switched on heating element to the number of half cycles with switched off heating element is set smoothly in time and directly in dependence on the detected level of the mains power supply.

19. The dialysis machine of claim 14, further comprising a temperature sensor, wherein the heating control unit is configured to set a ratio of a number of half cycles with switched on heating element to a number of half cycles with switched off heating element based on a signal of the temperature sensor and the detected level of the mains AC voltage.

20. The dialysis machine of claim 19, wherein the heating control unit generates a control signal based on a signal of the temperature sensor which is superimposed on control signals for adapting the power to the detected level of the mains AC voltage.

21. The dialysis machine of claim 19, wherein the temperature sensor determines the temperature of the medical liquid to be heated.

22. The dialysis machine of claim 19, wherein the dialysis machine is a peritoneal dialysis machine and the heater is configured to heat dialysate.

23. The dialysis machine of claim 22, further comprising a cassette for controlling the flow of the medical liquid, the cassette being coupled to a coupling surface of the dialysis machine and comprising at least one pumping chamber of the pump, wherein the cassette comprises a heating region that is in contact with the heating element of the dialysis machine.

24. The dialysis machine of claim 23, comprising a temperature sensor provided in the coupling surface of the dialysis machine and contacting a temperature sensor region of the cassette located at the inflow or at the outflow of the heating region in order to measure the temperature of the medical liquid flowing in or out of the heating region of the cassette.

25. The dialysis machine of claim 22, further comprising a heating bag connected to the cassette, the heating element being arranged in a heating plate that contacts the heating bag, wherein a temperature sensor is arranged in the heating plate to contact the heating bag in order to measure the temperature of the medical liquid in the bag.

* * * * *

UNITED STATES PATENT AND TRADEMARK OFFICE
CERTIFICATE OF CORRECTION

| | | |
|---|---|---|
| PATENT NO. | : 9,555,181 B2 | Page 1 of 1 |
| APPLICATION NO. | : 14/179646 | |
| DATED | : January 31, 2017 | |
| INVENTOR(S) | : Frank L. Hedmann, Sven Sebesta and Ulrich Wernicke | |

It is certified that error appears in the above-identified patent and that said Letters Patent is hereby corrected as shown below:

On the Title Page

Column 1, insert item (30), after the second titled "Related U.S. Application Data":
-- Foreign Priority - December 9, 2010   (DE)................. 10 2010 053 973.2 --

Signed and Sealed this
Sixth Day of June, 2017

Michelle K. Lee
*Director of the United States Patent and Trademark Office*